(12) United States Patent
Dolmetsch et al.

(10) Patent No.: US 9,097,703 B2
(45) Date of Patent: Aug. 4, 2015

(54) LIGHT CONTROLLED PROTEIN DIMERIZATION IN CELLS

(75) Inventors: Ricardo E. Dolmetsch, Stanford, CA (US); Masayuki Yazawa, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 468 days.

(21) Appl. No.: 13/499,201

(22) PCT Filed: Sep. 28, 2010

(86) PCT No.: PCT/US2010/050584
§ 371 (c)(1),
(2), (4) Date: Jun. 4, 2012

(87) PCT Pub. No.: WO2011/041327
PCT Pub. Date: Apr. 7, 2011

(65) Prior Publication Data
US 2012/0237966 A1    Sep. 20, 2012

Related U.S. Application Data

(60) Provisional application No. 61/278,069, filed on Oct. 1, 2009.

(51) Int. Cl.
| | | |
|---|---|---|
| *C12N 15/11* | (2006.01) | |
| *C12N 15/62* | (2006.01) | |
| *C12N 15/70* | (2006.01) | |
| *C12N 15/79* | (2006.01) | |
| *C12N 15/00* | (2006.01) | |
| *G01N 33/50* | (2006.01) | |
| *A61K 38/00* | (2006.01) | |

(52) U.S. Cl.
CPC ............ *G01N 33/5008* (2013.01); *C12N 15/00* (2013.01); *C07K 2319/70* (2013.01)

(58) Field of Classification Search
CPC .................................................... C12N 15/102
See application file for complete search history.

(56) References Cited

U.S. PATENT DOCUMENTS

| | | | |
|---|---|---|---|
| 7,220,552 B1 | 5/2007 | Crabtree et al. | |
| 8,809,259 B2 * | 8/2014 | Berry et al. | 514/1.1 |
| 2008/0311681 A1 * | 12/2008 | Johannsen et al. | 436/548 |

FOREIGN PATENT DOCUMENTS

WO    WO 9949064 A2 *    9/1999

OTHER PUBLICATIONS

Cheng et al. (2003) Functional conservation of light, oxygen, or voltage domains in light sensing, Proc. Natl. Acad. Sci., vol. 100, No. 10, pp. 5938-5943.*
Huq et al. (2000) GIGANTEA is a nuclear protein involved in phytochrome signaling in Arabidopsis, Peoc. Natl. Acad. Sci. USA, vol. 97, pp. 9789-9794.*
Auerbach; et al. "Drug Discovery, Using Yeast as a Model System: A Functional Genomic and Proteomic View", Curr Proteomics (2005), 2:1-13.
Ceriani; et el. "Light-dependent sequestration of Timeless by Cryptochrome", Science (Jul. 1999), 285 (5427):553-556.
Chelsky; et al. "Sequence requirements for synthetic peptide-mediated translocation to the nucleus", Mol Cell Biol (Jun. 1989); 9(6):2487-2492.
Levskaya; et al. "Spatiotemporal control of cell signalling using a light-switchable protein interaction", Nature (Oct. 2009); 461(7266):997-1001.
Nelson; et al. "FKF1, a clock-controlled gene that regulates the transition to flowering in *Arabidopsis*", Cell (Apr. 2000), 101(3):331-340.
Nelson; et al. "FKF1 [*Arabidopsis thaliana*]", GenBank Accession No. AAF32298 (May 2000) [Retrieved from the Internet Feb. 7, 2011: <http://www.ncbi.nlm.nih.gov/protein/AAF32298.2>].
Park; et al. GIGANTEA [*Arabidopsis thaliana*]. GenBank Accession No. AAF00092 (1999). [Retrieved from the Internet Feb. 7, 2011: <http://www.ncbi.nlm.nih.gov/protein/AAF00092.1>].
Sawa; et al. "FKFl and GIGANTEA complex formation is required for day-length measurement in *Arabidopsis*", Science (Oct. 2007), 318(5848):261-265.
Yazawa, et al. "Induction of protein-protein interactions in live cells using light", Nat Biotechnol (Oct. 2009), 27(10)-941-945.

\* cited by examiner

*Primary Examiner* — Manjunath Rao
*Assistant Examiner* — Samuel Liu
(74) *Attorney, Agent, or Firm* — Bozicevic, Field & Francis LLP; Pamela J. Sherwood

(57) ABSTRACT

Compositions and methods for light controlled protein-protein interactions in a living cell. Two interacting PICL (protein interaction controlled by light) polypeptides are provided. The first polypeptide comprises an LOV (Light, Oxygen or Voltage) domain, which domain is a light sensor that uses flavin mononucleotide (FMN) as a chromophore. The second polypeptide, specifically interacts with the L polypeptide upon light activation of the LOV domain. One or both of the polypeptides are fused to a cellular protein of interest. Upon exposure to light, a targeted interaction between cellular proteins occurs. The ability to regulate protein-protein interactions with subcellular resolution using light is useful for controlling biochemical processes such as transcription, receptor activation, protein degradation, synapse formation, etc. in cells and animals.

17 Claims, 11 Drawing Sheets

LIGHT CONTROLLED PROTEIN DIMERIZATION IN CELLS

BACKGROUND OF THE INVENTION

Light has a number of advantages as a stimulus to control molecular events; it has few off-target effects, it can be focused with subcellular resolution, and it can be rapidly modulated. Several technologies have been developed recently that use light-sensitive proteins to control electrical activity, cyclic AMP production and activation of G-protein coupled receptors in mammalian cells. However, although these technologies have revolutionized our study of these processes, they are not easily applied to the study of the majority of signal transduction cascades that depend on protein-protein interactions for function.

Cellular signaling pathways are part of a complex system of communication that governs basic cellular activities and coordinates cell actions. The ability of cells to perceive and correctly respond to their microenvironment is the basis of development, tissue repair, and immunity as well as normal tissue homeostasis. Errors in cellular information processing may be responsible for diseases such as cancer, autoimmunity, and diabetes. Understanding and manipulating cellular signaling pathways can provide mechanisms for drug screening assays, and for an understanding of important disease processes.

Signaling pathways, or signal transduction pathways, are often dependent upon an initial binding event, for example between a ligand and a cell-surface or cytoplasmic receptor, followed by protein-protein interactions in a network. In many examples, the initial binding event or the proximity of two interacting proteins in a pathway is sufficient to produce a biological effect of interest. Often, the behavior of a chain of interacting cellular proteins is altered following receptor activation. Research in signaling pathways may involve studying the spatial and temporal dynamics of receptors, and the components of signaling pathways that are activated by receptors, in various cell types.

Complex multi-component signal transduction pathways provide opportunities for feedback, signal amplification, and interactions inside one cell between multiple signals and signaling pathways. These systems are important in determining the biological effect of a perturbation, such a candidate drug or therapeutic modality. Indeed, pharmaceutical drug discovery, a multi-billion dollar industry, involves the identification and validation of therapeutic targets, as well as the identification and optimization of lead compounds. Desirable compound screening methods need to allow for both high throughput so that many individual compounds can be tested; and to provide biologically relevant information so that there is a good correlation between the information generated by the screening assay and the pharmaceutical effectiveness of the compound.

The development of screening assays and methods of easily manipulating protein interactions can provide better, faster and more efficient prediction of mechanisms of action, cellular effects and clinical drug performance. This issue is of great interest in a number of fields, and is addressed in the present invention.

SUMMARY OF THE INVENTION

Compositions and methods are provided for light controlled protein-protein interactions in a living cell. The systems of the invention provide a genetically encoded pair of polypeptides, which have a light-controlled interaction. One or both of the interacting polypeptide can be fused to a cellular protein of interest, thereby creating a light controlled interaction for the cellular protein or proteins. The system of the invention provides methods for light controlled transcription events; light controlled cellular localization events; light controlled signal receptor mediated signaling pathways; and the like. The systems of the invention are readily adapted to control multiple signaling events in cells, and are widely applicable for many applications in cellular and organismal biology.

In some embodiments of the invention, one or more genetic constructs are provided, which comprise two interacting PICL (protein interaction controlled by light) polypeptides, where each coding sequence may be on the same or a different vector.

The first polypeptide, which for convenience is referred to herein as the "L polypeptide" comprises an LOV (Light, Oxygen or Voltage) domain, which domain is a light sensor found in many plant proteins that use flavin mononucleotide (FMN) as a chromophore. In some aspects the L polypeptide may be a specifically modified FKF1 (Flavin-binding, Kelch repeat, F-Box 1) polypeptide, as described herein. The second polypeptide, which for convenience is referred to herein as the "I polypeptide" specifically interacts with the L polypeptide upon light activation of the LOV domain. In some aspects, the I polypeptide is a specifically modified GI protein, as described herein. Modifications of interest for the L and the I polypeptide include localization signals; detectable labels that are optionally genetically encoded; and genetic alterations to decrease background levels of interaction between the two polypeptides. The genetic constructs of the invention may include suitable promoters, integration sequences, convenient restriction or priming sites for insertion of fusion partners; and the like. The constructs may be provided in a kit form, for example including reagents and buffer for utilizing the constructs in building an interacting system with proteins of interest.

In other embodiments of the invention, polypeptides are provided. The polypeptides may comprise an L polypeptide or an I polypeptide, and may be fused to a cellular protein of interest. The present invention also provides a composition comprising a cell, wherein the cell comprises genetic constructs of the invention, and/or polypeptides of the invention.

In other embodiments, screening methods are provided, which screening methods utilize two interacting PICL (protein interaction controlled by light) polypeptides of the invention. Such methods include contacting a cell with a candidate agent, for example a drug candidate, where the activity of the agent during a cellular process mediated by protein-protein interaction is of interest. The targeted cell is genetically modified to express an L polypeptide and an I polypeptide of the invention, where one or both of the polypeptides are fused to a cellular protein of interest. The targeted cell is exposed to light in order to induce the protein interaction and cellular event, and the activity of the agent during the process is determined.

The ability to regulate protein-protein interactions with subcellular resolution using light is useful for controlling biochemical processes such transcription, receptor activation, protein degradation, synapse formation, etc. in cells and animals. In various embodiments, the PICL polypeptides are used to confer light-dependent regulation to a transcription factor, by fusion of the PICL polypeptide to a DNA binding domain. The formation of specialized cellular structures such as synapses is induced at particular locations by creating PICL fusions of synaptic proteins and using focused light to induce their interaction. Fusion of PICL tags to the cytoplasmic domains of receptor tyrosine kinases provides a system for the light activation of specific receptors using light.

This and other embodiments of the invention will be described in detail hereinafter.

DETAILED DESCRIPTION OF THE EMBODIMENTS

Figure 1:
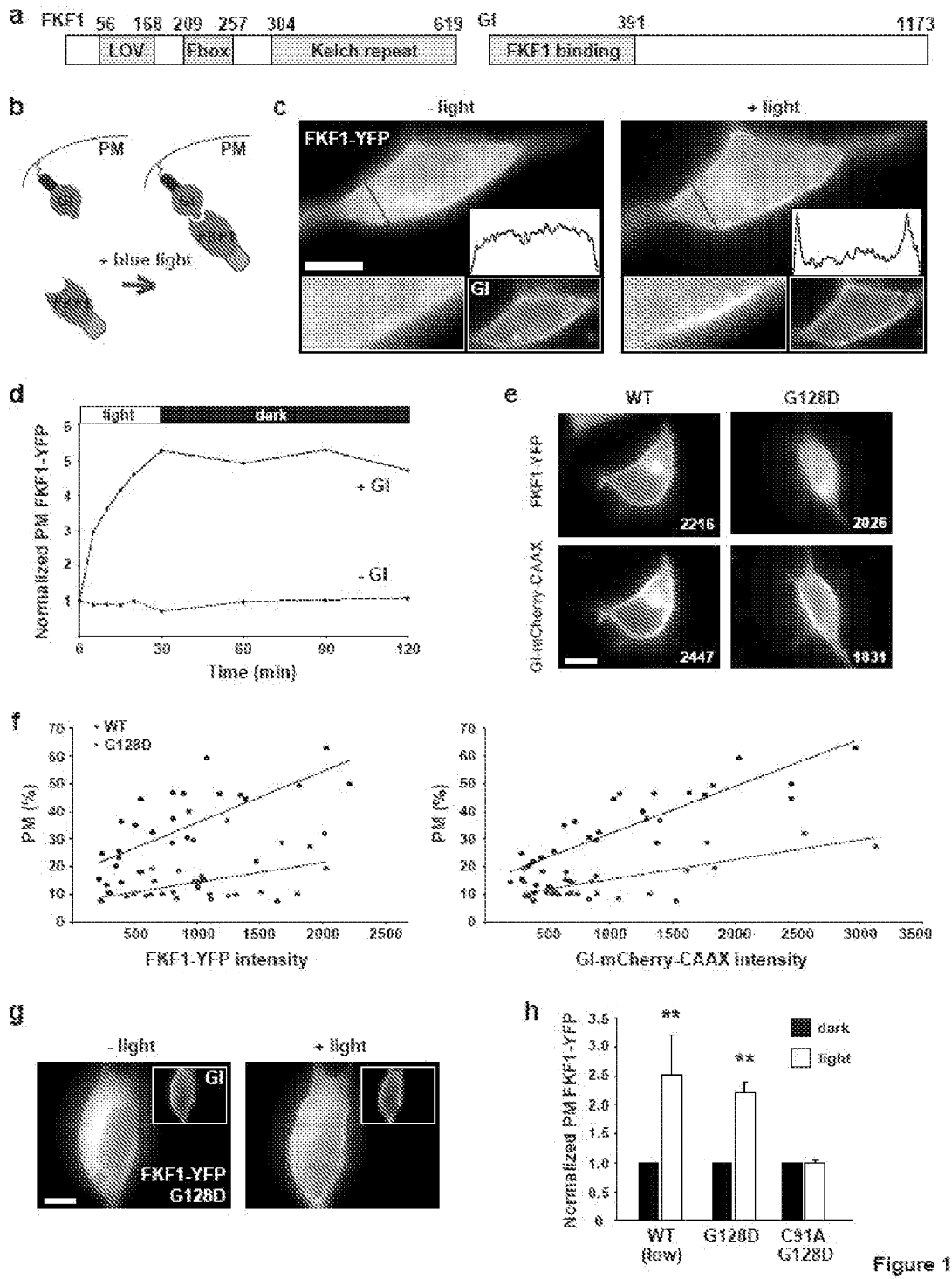
FIG. 1. GI and FKF1 interact in response to blue light. a) Schematic of FKF1 and GI showing FKF1 LOV domain and putative GI FKF1 binding region. b) Schematic representation of light-induced recruitment of FKF1-YFP to GI-mCherry-CAAX localized to the plasma membrane. c) Images of NIH 3T3 cell expressing FKF1-YFP and GI-mCherry-CAAX (right bottom inset) before and 20 minutes after blue light illumination. A magnified image of the cell membrane (left inset) and a line profile (right above inset) are shown. Representative cell, n=50. Scale bars=10 µm. d) Time course of light-induced FKF1-YFP translocation to the plasma membrane with (solid) and without (dashed) GI-mCherry-CAAX. The Y axis shows the fraction of FKF1-YFP at the plasma membrane normalized to the value before illumination. e) NIH 3T3 cells expressing high levels of either FKF1-YFP WT or the FKF1-YFP G128D (top panels) mutant along with GI-mCherry-CAAX (bottom panels) before illumination with blue light. Images were collected using identical camera settings and the numbers indicate the average intensity of YFP and mCherry in these cells. f) Graphs of plasma membrane-localized FKF1-YFP (black) or FKF1-YFP G128D mutant (red) in single cells as a function of FKF1-YFP or GI-mCherry-CAAX before illumination. Black and red lines are regression fits for the plots of FKF1-YFP WT and G128D, respectively. There was no significant correlation between the PM population of FKF1-YFP G128D and the expression of GI-mCherry-CAAX (rs=0.342) or FKF1-YFP G128D (rs=0.343) whereas there was a significant correlation between the PM localization of FKF1-YFP WT and both the expression of GI-mCherry-CAAX (rs=0.858) and of FKF1-YFP (rs=0.704). g) Images of cells expressing FKF1-YFP G128D before and 30 minutes after illumination with blue light. h) Measurements of the amount of FKF1-YFP at the cell membrane in cells expressing either WT FKF1, G128D FKF1, or C91A G128D FKF1 before and after 30 minutes of illumination with blue light (mean±s.e.m. n=5. **P<0.01). The WT bar includes only cells expressing low levels of FKF1 and GI, in which translocation was observed.

The present invention provides a set of tools for controlling the activity of proteins that initiate a cellular process through protein-protein interaction. The system of the invention provides methods for light controlled transcription events; light controlled cellular localization events; light controlled signal receptor mediated signaling pathways; and the like.

The systems of the invention are readily adapted to control multiple signaling events in cells, and are widely applicable for many applications in cellular and organismal biology. Specific examples set forth herein include, without limitation, light controlled transcription mediated by Gal4, based on the widely-used Gal4-VP16 system. The PICL Gal4 system allows the use of light to activate the expression of a gene in single cells, including animals such as mammals, and *Drosophila* (in which a large number of UAS-driven lines have been established). Specific examples also include light controlled signaling pathways mediated by Rac1. Rac1 is a key initiator of a wide variety of biological events including dendritic spine formation in neurons, B and T cell development and cardiac growth and hypertrophy. PICL Rac1 is extremely useful for controlling dendritic spines formation with temporal and spatial precision, for regulating immune development and for controlling cardiovascular function in live animals.

PICL has several advantages relative to existing methods for controlling protein-protein interactions. The L polypeptide utilizes flavin-mononucleotide as a chromophore, which is widely available inside cells, and thus does not require introduction of an exogenous agent. Unlike soluble molecules that must be administered systemically to animals or applied to cells in a bath, light can be delivered with great spatial and temporal precision allowing selective control of protein interactions in single cells or in subcellular domains. Preferred L polypeptides of the invention are activated by blue light, at about 450 nm wavelength, which produces little toxicity and has few off-target effects in most cells. The possibility of light-induced toxicity is further decreased in the systems of the invention by the unexpected finding that the interaction between the L polypeptide and the I polypeptide reverses slowly, thus the protein interaction induced by light remains stable for at least about 1 hour, at least about 2 hours, or more, hours, reducing the need for continuous exposure of cells to blue light. Finally, the PICL system is simple to use in intact organisms, and only requires equipment such as microscopes and lamps that are widely available in biological laboratories.

The invention is suitable for use with any cell type or tissue, including microbial cells, insect cells, yeast cells, mammalian cells including primary cells, normal and transformed cell lines, transduced cells and cultured cells. These may be derived from all sources, and with respect to species, e.g., human, simian, rodent, etc. Intact tissues and animals, particularly laboratory test animals, may find use. Cells may be genetically altered, e.g. by transfection or transduction with recombinant genes or by antisense technology. Methods for generating genetically modified cells are known in the art, see for example "Current Protocols in Molecular Biology", Ausubel et al., eds, John Wiley & Sons, New York, N.Y., 2000.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford IL.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

"Optional" or "optionally" means that the subsequently described event of circumstances may or may not occur, and that the description includes instances where said event or circumstance occurs and instances in which it does not.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Preferred dosages for a given compound are readily determinable by those of skill in the art by a variety of means.

Definitions

Interaction. As used herein, interaction refer to two domains or independent polypeptide entities that exhibit sufficient physical affinity to each other so as to bring the two "interacting" domains or entities physically close to each other. An extreme case of interaction is the formation of a chemical bond that results in continual, stable proximity of the two domains. Interactions that are based solely on physical affinities, although usually more dynamic than chemically bonded interactions, can be equally effective at co-localizing independent entities. Examples of physical affinities and chemical bonds include but are not limited to, forces caused by electrical charge differences, hydrophobicity, hydrogen bonds, van der Wals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include the specific interactions described herein between the L polypeptide and I polypeptide, e.g. utilizing the interacting sequences set forth in SEQ ID NO:3 and SEQ ID NO:6.

Illumination, as used herein, refers to various methods known in the art for irradiating a target cell, tissue or organism with light of a particular wavelength. For purposes of the invention, blue light, for example light at a wavelength of about 450 nm, may be used. The light source may be a laser, including two photon lasers, optical fiber, etc. Focused light beams may used, e.g. to activate protein interaction at a subcellular location, such as with an axon of a neuron, a region of a muscle fiber, and the like.

L polypeptide. The L polypeptide of the invention comprises a Light, Oxygen or Voltage (LOV) domain, which is a light sensor found in many plant proteins that uses flavin mononucleotide (FMN) as its chromophores. FMN is a derivative of riboflavin (vitamin B2) that functions as a prosthetic group for various oxydoreductases including NADH dehydroxygenase and is widely available in eukaryotic cells. In the methods of the invention the L polypeptide may be fused to a target protein of interest, however the L-polypeptide itself, and particularly genetic constructs encoding the L polypeptide, also find use.

In certain embodiments of the invention, the L polypeptide is derived from the *Arabidopsis thaliana* protein FKF1. Illumination of FKF1 with 450 nm (blue) light induces formation of a covalent bond between FMN and cysteine 91 in the protein (residue numbered from the wild-type protein), causing a conformational change in FKF1 that allows it to bind to GI. The cysteinyl-flavin bond is subsequently hydrolyzed returning the LOV domain to its resting state, causing the FKF1-GI complex to dissolve. The wild-type polypeptide sequence may be accessed at Genbank, accession number AAF32298, and is provided herein as SEQ ID NO:1 and SEQ ID NO:2. The FKF1 domain involved in light activated interaction is set forth in SEQ ID NO:3. As used herein, a "domain" includes any region of a polypeptide that is responsible for selectively assembling with an assembly partner of interest. When two domains assemble with each other, they meet at a protein-protein interaction interface.

L polypeptides of the invention usually comprise at least the amino acid sequence set forth in SEQ ID NO:3, usually comprising at least one amino acid modification to reduce background interaction.

The interaction between domains of FGF1 and GI (i.e. SEQ ID NO:3 and SEQ ID NO:4) is undesirably high in the absence of light activation. To reduce this interaction, point mutations are introduced into the interacting domain or domains are introduced, which reduce basal levels of interaction without substantially reducing light induced interaction. Without limitation, mutations of interest in SEQ ID NO:3 include substitutions other than leucine at residue 120; substitutions other than glycine at residue 128, substitutions other than leucine at residue 120, substitutions other than glutamine at residue 129, and substitutions at residues 50-55 to other than the wild-type sequence. Specific mutations include L120S, L120D, G128D, G128A, E129A, E129K. G128D, or G128E are of particular interest.

The L polypeptide may include additional FKF1 sequences other than those of SEQ ID NO:3; however where other sequences are included the protein may be modified from the wild-type to reduce basal levels of nuclear localization, by disrupting nuclear localization sequences (NLS). Methods of identifying identify NLS sequences are known in the art, for example see the PSORT II prediction program. The NLS sequence of FKF1 is found within SEQ ID NO:2, residues 13-16. Any sequence modification that disrupts the NLS sequence may be used, e.g. deletion, substitution, etc. In some embodiments, residues 13-16 are deleted. In other embodiments, the lysine residue at position 15 is substituted with an amino acid other than lysine, e.g. serine, threonine, valine, alanine, etc.

Additional optional sequences that may be included in the L polypeptide include localization signal for a cellular site. In some embodiments, such a localization signal is a CAAX box, or any other membrane localization signal. Membrane localization may be of interest in some applications where the target protein is a cell surface receptor or channel.

A detectable marker is optionally included in the L polypeptide. Many such markers are known in the art and need not be described in detail here. Non-limiting examples include various fluorescent proteins, e.g. mCherry, green fluorescent protein, GFP, sgGFP, sgBFP, BFP blue shifted GFP (Y66H), Blue Fluorescent Protein, CFP (Cyan Fluorescent Protein), Cyan GFP, DsRed, monomeric RFP, EBFP, ECFP, EGFP, GFP (S65T), GFP red shifted (rsGFP), GFP wild type, non-UV excitation (wtGFP), GFP wild type, UV excitation (wtGFP), GFPuv, HcRed, rsGFP, Sapphire GFP, sgBFP, sgBFP (super glow BFP), sgGFP, sgGFP (super glow GFP), wt GFP, Yellow GFP, YFP, and the like.

I polypeptide. The I polypeptide of the invention specifically interacts with the L polypeptide upon light activation of the LOV domain. In certain embodiments of the invention, the L polypeptide is derived from the *Arabidopsis thaliana* protein Gigantea (GI). The wild-type polypeptide sequence may be accessed at Genbank, and is provided herein as SEQ ID NO:4 and SEQ ID NO:4. The domain involved in FKF1 interaction is set forth in SEQ ID NO:6.

L polypeptides of the invention usually comprise at least the amino acid sequence set forth in SEQ ID NO:6. As with the L polypeptide, the sequence may be mutated to reduce basal levels of interaction, however it is not necessary that both polypeptides comprise such a mutation, and therefore the wild-type sequence may be used for the purposes of the invention.

The I polypeptide may include additional GI sequences other than those of SEQ ID NO:6. Where other sequences are included the protein may be modified from the wild-type to reduce basal nuclear localization, by disrupting nuclear localization sequences (NLS). Methods of identifying identify NLS sequences are known in the art, for example see the PSORT II prediction program. The NLS sequence of FKF1 is found within SEQ ID NO:2, residues 607-610. Any sequence modification that disrupts the NLS sequence may be used, e.g. deletion, substitution, etc. In some embodiments, residues 607-610 are deleted. In other embodiments, the lysine residue at position 607 is substituted with an amino acid other than lysine, e.g. serine, threonine, valine, alanine, etc.

Additional optional sequences that may be included in the I polypeptide include localization signal for a cellular site. In some embodiments, such a localization signal is a CAAX box, or any other membrane localization signal. Membrane localization may be of interest in some applications where the target protein is a cell surface receptor or channel. A detectable marker is also optionally included in the I polypeptide, as described above.

The term "fusion protein" refers to a non-naturally occurring hybrid or chimeric protein having two or more distinct portions covalently linked together, each portion being or being derived from a specific molecule, and also refers to the nucleic acid sequence encoding the same. One or both of the L polypeptide and I polypeptide may be fused to a target protein of interest.

The present invention contemplates the use of any protein of interest for fusion to the light controlled polypeptides of the invention. Thus, the target polypeptide may be any protein of interest or portion thereof to which another polypeptide interacts. For example, the polypeptide may be receptors, including tyrosine kinase receptors, transcription factors, G-proteins, Alzheimer's amyloid peptide (Aβ), SOD1, presenillin 1 and 2, renin, α-synuclein, amyloid A, amyloid P, activin, anti-HER-2, bombesin, enkephalinase, protease inhibitors, therapeutic enzymes, α1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as αFGF and βFGF), insulin-like growth factor-I and -II, des(1-3)-IGF-I (brain IGF-I), insulin-like growth factor binding proteins, nerve growth factor (such as NGF-β), platelet-derived growth factor (PDGF), vascular endothelial growth factor (VEGF), receptors for growth hormones or growth factors, transforming growth factor (TGF) (such as TGF-α, TGF-β1, TGF-β2, TGF-β3, TGF-β4 or TGF-β5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin β-chain, insulin receptor, proinsulin, luteinizing hormone, integrin, interleukins (ILs) (such as IL-1 to IL-10, IL12, IL-13), erythropoietin, thrombopoietin, fibrillin, follicle stimulating hormone, clotting factors (such as factor VIIIC, factor IX, tissue factor, and von Willebrands factor, anti-clotting factors (such as Protein C, atrial naturietic factor, lung surfactant), a plasminogen activator (such as human tissue plasminogen activator or urokinase), thrombin, tumor necrosis factor-α or β, α-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-α, -β and -γ), keratin, osteoinductive factors, PRNP, regulatory proteins, superoxide dismutase, surface membrane proteins, transport proteins, T-cell receptors, viral antigens such as a portion of the AIDS envelope, immunoglobulin light chain, antibodies, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, gp120, p300, CREB, AP1, ras, rac, NFAT, jun, fos, dentaorubral pallidoluysian atrophy-associated protein, a microbial protein (e.g., maltose binding protein, ABC transporter, glutathione S transferase, thioredoxin, β-lactamase), and the like, or derivatives or active fragments or genetic variants of any of the peptides listed above. The polypeptides may be native or mutated polypeptides, and sources for mammalian polypeptides include, but are not limited to, human, bovine, equine, porcine, lupine and rodent sources, however various other species also find use, e.g. *Drosophila, Saccharomyces, C. elegans*, etc.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of a sample (e.g., a nucleic acid encoding a fusion protein of the present invention) to a desired cell or tissue.

As used herein, the term "site-specific recombination target sequences" refers to nucleic acid sequences that provide recognition sequences for recombination factors and the location where recombination takes place.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics (e.g., increased or decreased solubility) when compared to the wild-type gene or gene product.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention is not limited to naturally occurring protein molecules. For example, the present invention includes synthesis of fusion proteins comprising multiple regions of unique polypeptide sequences (e.g., an L or I polypeptide as defined herein, a target protein sequence, and marker protein sequence).

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "test compound" and "candidate compound" refer to any chemical entity, pharmaceutical, drug, and the like that is a candidate for use to alter (e.g., enhance or inhibit) the interaction between two or more molecules (e.g., peptides or proteins). Test compounds comprise both known and potential therapeutic compounds. A test compound can be determined to be therapeutic by screening using the screening methods of the present invention. Examples of test compounds include, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, drug, antibody, prodrug, antibodies or portions thereof (e.g., antibody fragments), glycopeptides, glycoproteins, proteoglycans and the like, and synthetic analogues or derivatives thereof, including peptidomimetics, small molecule organic compounds and the like, and mixtures thereof.

As used herein, the term "test compound library" refers to a mixture or collection of one or more compounds generated or obtained in any manner. Preferably, the library contains more than one compound or member. The test compound libraries employed in this invention may be prepared or obtained by any means including, but not limited to, combinatorial chemistry techniques, fermentation methods, plant and cellular extraction procedures and the like. Methods for making combinatorial libraries are well-known in the art (See, for example, E. R. Felder, Chimia 1994, 48, 512-0541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Each of these references is incorporated herein by reference in its entirety).

The term "synthetic small molecule organic compounds" refers to organic compounds generally having a molecular weight less than about 1000, preferably less than about 500, which are prepared by synthetic organic techniques, such as by combinatorial chemistry techniques.

As used herein; the term "drug" refers to a pharmacologically active molecule that is used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "host cell" refers to any cell, whether located in vitro or in vivo, that can be, or has been, a recipient for or incorporates exogenous nucleic acid sequences (e.g., vectors comprising fusion protein sequence), polynucleotides and/or proteins of the present invention. It is also meant to include progeny of a single cell, and the progeny may not necessarily be completely identical (e.g., in morphology or in genomic or total DNA complement) to the original parent cell due to natural, accidental, or deliberate mutations. The cells may be eukaryotic or prokaryotic and include, but are not limited to bacterial cells (e.g., E. coli), yeast cells, mammalian cells, avian cells, amphibian cells, plant cells, fish cells, and insect cells).

Methods

Methods of the invention utilize the light activated interaction between the L polypeptide and the I polypeptide to provide for controlled protein interactions in a cell. As discussed above, the illumination of the L polypeptide with a suitable light causes a molecular change that allows stable binding to the I polypeptide. The interaction finds particular use when one or both of the PICL polypeptides are fused to a target protein or proteins. By fusing a target protein to a PICL "tag", the property of light induced interaction may be conferred on the protein.

In one embodiment, the PICL system is used to direct light induced localization of a protein to a desired site in the cell. In such methods, the target protein is fused to the L polypeptide; while the I polypeptide is fused to a cellular sorting signal, e.g. with a membrane localization signal, with a lysosome sorting signal, a mitochondrial sorting signal, etc., as are known in the art. Upon illumination, the target protein is carried to the desired location by the L polypeptide interacting with the I polypeptide. Such embodiments are exemplified herein by the fusion of a small GTPase to the L polypeptide, and by localizing the I polypeptide to the cell membrane. The membrane localization of the GTPase following illumination is shown to activate specific signaling pathways.

In one embodiment, the PICL system is used to induce interaction between two polypeptides in a cell. In such methods one protein of interest is fused to the L polypeptide, and the other is fused to the I polypeptide. Upon illumination, the two target polypeptides are brought together by the light induced interaction of the L and I polypeptides. Such embodiments are exemplified herein by the fusion of a transcription factor to one of the PICL polypeptides, and fusing a transactivation domain to the other PICL protein. In this particular example, nuclear localization was maintained for both PICL polypeptides. The interaction of the transcription factor and transactivation domain following illumination is shown to activate transcription.

One of skill in the art will readily perceive that many cellular processes are initiated by the interaction of two proteins, or by the movement of a protein to a specific site in a cell. Thus, the vectors and polypeptides of the invention are easily adapted to act as light "transducers" in any process or target polypeptide of interest.

Vectors encoding one or both of the PICL polypeptides are provided, and may also include various selectable markers, cloning sites, origins of replication, promoters, packaging signals, recombination signals, etc., for more convenient insertion of localization signals, coding sequences of target proteins, and the like.

One of skill in the art is further informed as to method for introducing genetic constructs and vectors into cells, and for the construction of transgenic animals comprising such vectors.

Some specific uses of the methods of the invention include light activation of a pathway of interest for compound screening. In such methods, the PICL polypeptides are utilized as described above to bring about a protein-protein interaction or a protein translocation, which light activated event results in activation of a cellular process in a host cell.

Test compounds can be applied to host cells (e.g., in vivo or in vitro) at varying dosages, and the response of these cells monitored (e.g., for growth over various time periods). Physical characteristics of these cells can be analyzed by observing cells by microscopy. The induction of expression of new or increased levels of proteins such as enzymes, receptors and other cell surface molecules can be analyzed with any technique known in the art. Thus, host cells of the present invention can be used to determine the effect of test compounds (e.g., small molecule inhibitors, pharmaceuticals, biological agents, etc.) in the presence of a desired biological activity.

In some embodiments, test compounds can be solubilized and added to host cells (e.g., in vitro (e.g., in the culture medium), or, in vivo (e.g., to a recipient subject that has received a host cell graft). In some embodiments, various concentrations of the test compound are utilized to determine an efficacious dose. In some embodiments, administration of the test compound is consistent over a period of time (e.g., administered one, two or more times a day) so as to keep the concentration of the test compound constant.

Test compounds can be administered in vitro or in vivo at a variety of concentrations. For example, in some embodiments, test compounds are added to culture medium or to a subject so as to achieve a concentration from about 10 pg/ml to 10 mg/ml, or from about 1 ng/ml (or 1 ng/cc of blood) to 100 ng/ml (or 100 ng/cc of blood), although higher (e.g., greater than 10 mg/ml) and lower (e.g., less than 10 pg/ml) concentrations may also be used.

The effects of a test compound can also be identified on the basis of a significant difference relative to a control regarding criteria such as the ratios of cell viability, proliferation rate, number of host cells, host cell alterations in gene expression and expressed phenotypes.

It is contemplated that a successfully identified test compound (e.g., a test compound, analogue or mimetic identified that is capable of providing a desired effect can be utilized in a pharmaceutical composition, e.g., to be administered to a subject. Thus, the compositions can also be prepared as injectables, either as liquid solutions or suspensions; solid forms suitable for solution in, or suspension in, liquid prior to injection may also be prepared.

In many drug screening programs that test libraries of compounds and natural extracts, high throughput assays are desirable in order to maximize the number of compounds surveyed in a given period of time. Screening assays of the present invention can be carried out in such a format, and accordingly may be used as a "primary" screen. In some embodiments, the approximate efficacy of the test compound can be determined by generating dose response curves from host cell data obtained using various concentrations of the test compound. Moreover, in some embodiments, a control assay is performed to provide a baseline for comparison. In the control assay, host cell growth is quantitated in the absence of the test compound.

Kits

Also provided are kits for practicing the subject methods. The kits according to the present invention may comprise: genetic sequences encoding an L polypeptide and an I polypeptide, which may be present on the same or different vectors, and may further comprise buffers, enzymes, and the like for insertion of a desired fusion partner; and (b) instructions for using the provided genetic constructs.

The various reagent components of the kits may be present in separate containers, or may all be precombined into a reagent mixture for combination with samples. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

Development of a Genetically Encoded System for Controlling Protein-Protein Interactions in Live Cells Using Blue Light Protein-protein interactions underlie activation of most signaling cascades in cells. We have developed a new technology called PICL (Protein Interactions Controlled by Light) to control protein hetero- and homo-dimerization in live cells using light. We modified FKF1 and GIGANTEA (GI) proteins from *Arabidopsis thaliana*, to generate protein tags whose interaction is controlled by blue light. We demonstrated the utility of this system by developing PICL constructs that can recruit the small G-protein Rac1 to the plasma membrane and generate local lamellipodia in response to focal illumination. We also generated a light-activated transcription factor by fusing domains of GI and FKF1 to the DNA-binding domain of Gal4 and to the transactivation-domain of VP16, showing that this technology is easily adapted to other systems. These studies set the stage for the development of light-regulated signaling molecules that can be used to control receptor activation, synapse formation and other signaling events in organisms.

Figure 5:
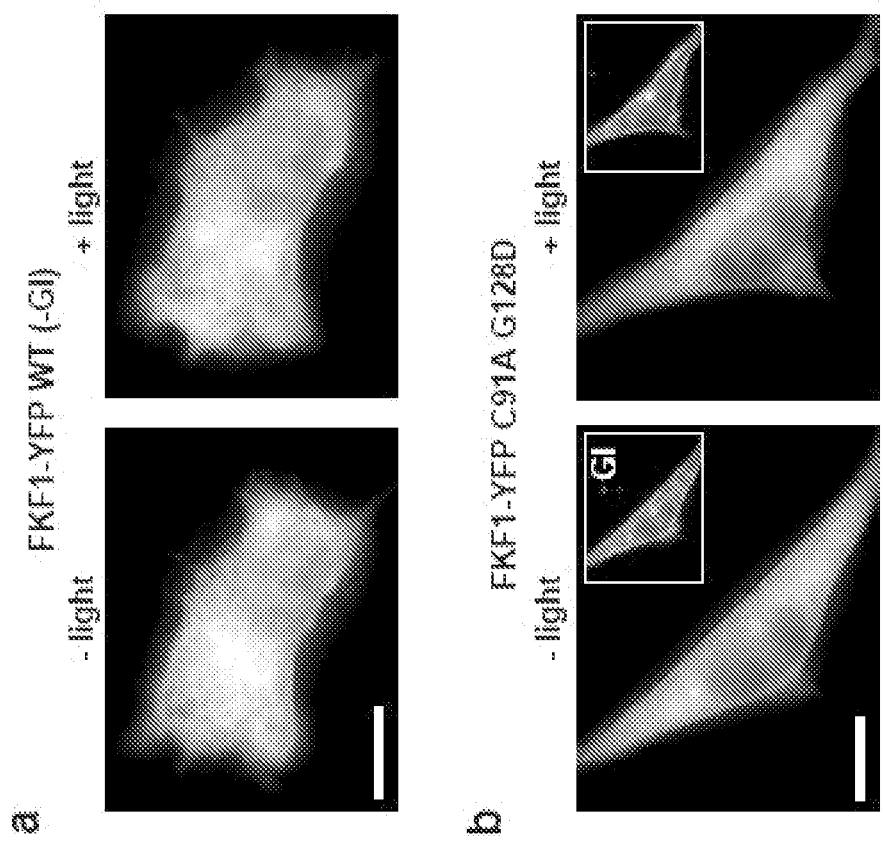
FIG. 5. Control experiments of FKF1 recruitment to the plasma membrane a) NIH 3T3 cells expressing FKF1-YFP without GI-mCherry-CAAX before and 20 minutes after illumination with blue light. b) Images of cells expressing FKF1-YFP G128D with C91A mutation that prevents light-sensitive binding to GI, before and 30 minutes after illumination with blue light. Scale bars=10 µm.

We investigated whether FKF1 and GI could be expressed in mammalian cells and whether the light-regulated interaction of these two proteins could be used to control the interaction of heterologous proteins in live cells. To examine the expression of FKF1 and GI in mammalian cells, we labeled the proteins with HA and FLAG epitope tags, introduced them into NIH 3T3 cells, and immunostained the cells with anti-epitope antibodies (FIG. 1a, b). We found that FKF1 and GI were well expressed and localized both in the nucleus and in the cytoplasm of cells, similar to what has been described for these proteins in plant cells. The nuclear localization of FKF1 and GI is undesirable in a system designed to control the interaction or function of cytoplasmic proteins using light. We therefore used the PSORT II prediction program to identify NLS sequences in both proteins (FKF1 aa 13-16 and GI aa 607-610; FIG. 5a), and disrupted these sequences by substituting threonines for the lysines at positions 15 of FKF1 (K15T) and 607 of GI (K607T). These two mutations significantly reduced the concentration of both proteins in the nucleus (FIG. 1a, b and FIG. 5b), allowing us to study light-induced interactions exclusively in the cytoplasm of mammalian cells.

To determine whether FKF1 and GI interact with each other in mammalian cells in response to blue light, we designed a strategy to visualize the recruitment of cytoplasmic FKF1 to a membrane-targeted GI in live cells (FIG. 1c). We first labeled GI with the fluorescent protein mCherry and targeted this protein to the cell membrane using the C-terminal farnesylation motif from K-Ras called the CAAX box. We then labeled FKF1 with YFP, introduced it into cells with GI-mCherry-CAAX, and measured the localization of both proteins using epifluorescence time-lapse microscopy. As expected, the CAAX box targeted GI-mCherry to the cell membrane, whereas FKF1-YFP remained cytoplasmic.

Upon illumination of the cells with 450 nm light, there was a significant increase in the amount of FKF1-YFP at the cell membrane in about 30% of the cells; this membrane recruitment was apparent within five minutes and increased for thirty minutes following light stimulation (FIGS. 1d and e). In contrast, cells expressing FKF1-YFP without GI-mCherry-CAAX did not show any increase in membrane fluorescence, suggesting that FKF1-YFP membrane recruitment depended on binding to GI-mCherry-CAAX (FIG. 1e and f). Interestingly, FKF1-YFP remained at the membrane for at least 1.5 hours after a thirty-minute exposure to weak blue light (FIG. 1e), consistent with studies demonstrating that the cysteinyl-flavin adduct of FKF1 has a long half-life at room temperature. These results indicate that FKF1 binds to GI in mammalian cells following a short exposure to light, and further suggests that these two proteins form a relatively stable complex that would be useful for activating signaling events that require prolonged protein-protein interactions.

Figure 2:
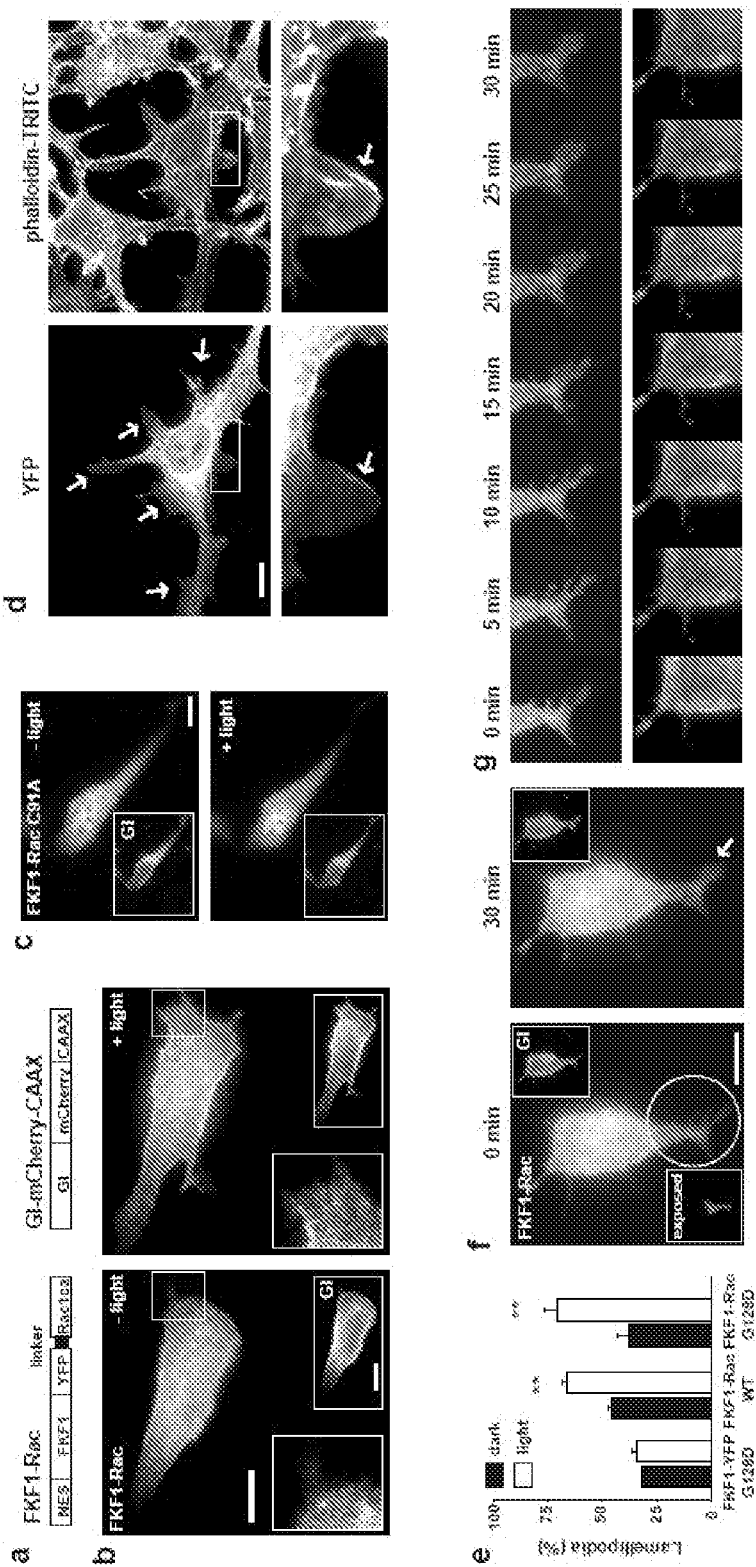
FIG. 2 Light-induced recruitment of FKF1-Rac1 to the plasma membrane and formation of lamellipodia. a) Schematics of fusion proteins used to generate blue light-regulated Rac1. The nuclear export signal (NES) and the linker (~15 aa) between YFP and the constitutively active Rac1 G12V mutant lacking the CAAX domain (Rac1ca) are indicated. b) NIH 3T3 cells expressing FKF1-YFP-linker-Rac1ca (FKF1-Rac) and GI-mCherry-CAAX before (left) and 25 minutes after a 5 minute exposure to blue light (right). Inset shows formation of lamellipodia in cells exposed to light. Scale bar=5 µm. c) NIH 3T3 cells expressing FKF1-Rac containing the C91A mutation that prevents blue light activation and the G128D mutation that reduces background binding show no response to blue light. d) Immunocytochemistry of cells expressing FKF1-Rac and GI-CAAX after blue light exposure using either anti-GFP antibodies to detect FKF1-Rac (left) or TRITC conjugated phalloidin to label polymeric and oligomeric forms of actin (right). Arrows indicate lamellipodia induced by FKF1-Rac translocation to the plasma membrane of the cell. Scale bar=5 µm. e) Quantification of the percent of transfected cells showing at least one lamellipodia before and two hours after a five minute exposure with blue light measure. Cells were transfected with FKF1-YFP, FKF1-Rac or FKF1-Rac G128D as indicated (mean±s.e.m. n=>170 in 4 independent experiments. **P<0.01). f) NIH 3T3 cell expressing FKF1-Rac and GI-mCherry-CAAX illuminated with a focal spot of light for 5 minutes. Images show the cell before and 30 minutes after stimulation (n=5). Scale bar=5 µm. g) Time lapse images of GI-mCherry-CAAX in the illuminated region (top) or in a region that was not illuminated (bottom) show an increase in lamellipodia in response to light.

The failure to detect light-inducible recruitment of FKF1 to the membrane in 70% of the cells suggested that this process is relatively inefficient. Close examination of the cells that did not show FKF1-YFP translocation to the membrane revealed that these cells expressed FKF1-YFP and GI-mCherry-CAAX at high levels and had membranous FKF1-YFP before illumination (FIG. 2a, left panels). Measurement of the expression of FKF1-YFP and GI-mCherry-CAAX, and of the amount of FKF1-YFP at the membrane in single cells (FIG. 2b, c, black symbols) confirmed that recruitment of FKF1-YFP to GI-mCherry-CAAX was strongly dependent on the concentration of both proteins suggesting, that when overexpressed, FKF1-YFP and GI-mCherry-CAAX have significant affinity for each other even in the absence of light.

Figure 6:
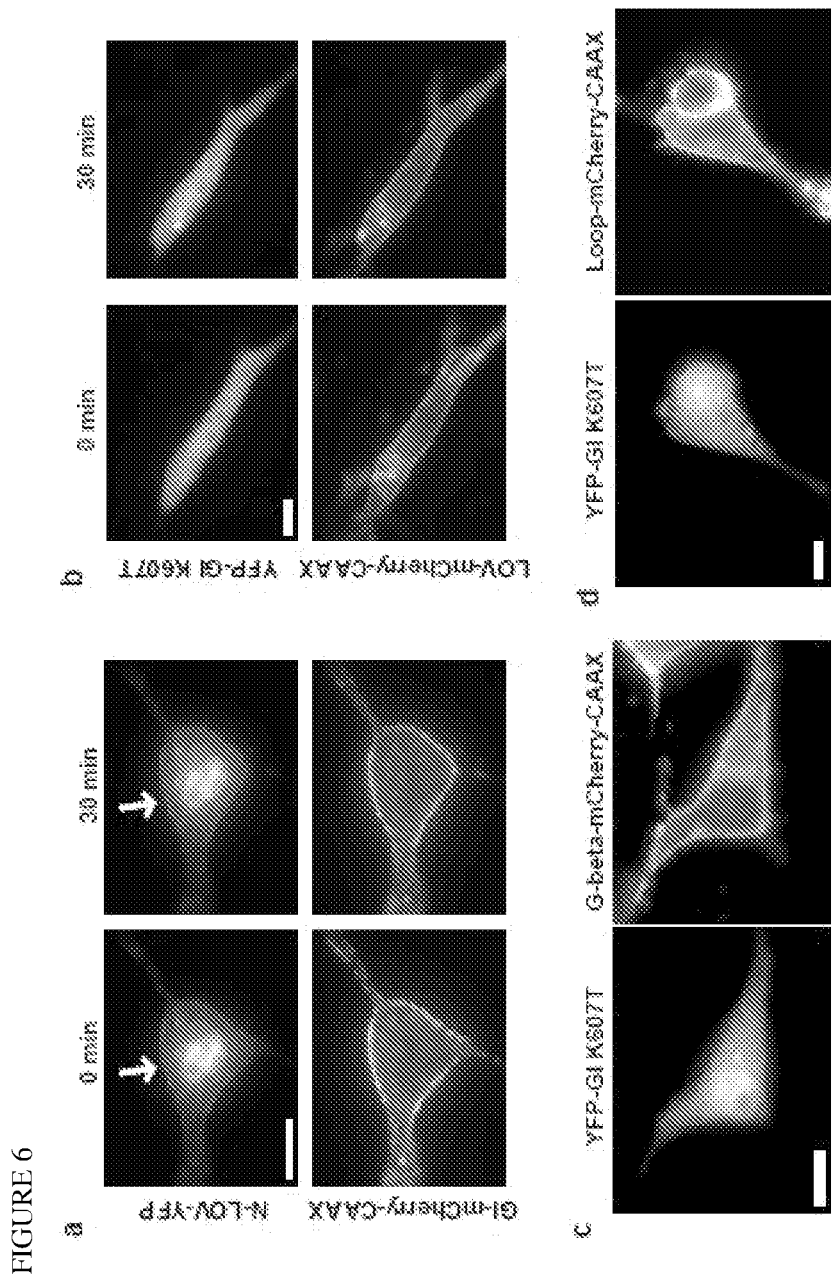
FIG. 6. Characterization of binding of FKF1 mutants to GI a) N-LOV-YFP doesn't show significant light-dependent binding to GI-mCherry-CAAX in NIH 3T3 cells and is localized in the nucleus. The arrows show basal binding of N-LOV-YFP to GI-mCherry-CAAX. b) LOV-mCherry-CAAX without the N-terminal domain does not recruit YFP-GI K607T before or after illumination. c) Cytoplasmic YFP- GI K607T does not bind to the G-beta-sheet-mCherry-CAAX suggesting that this region is not sufficient for interaction between FKF1 and GI. d) The Loop-mCherry-CAAX does not recruit YFP-GI K607T while FKF1-YFP without the Loop domain does not bind GI-mCherry-CAAX. Scale bars=10 µm.
Figure 7:
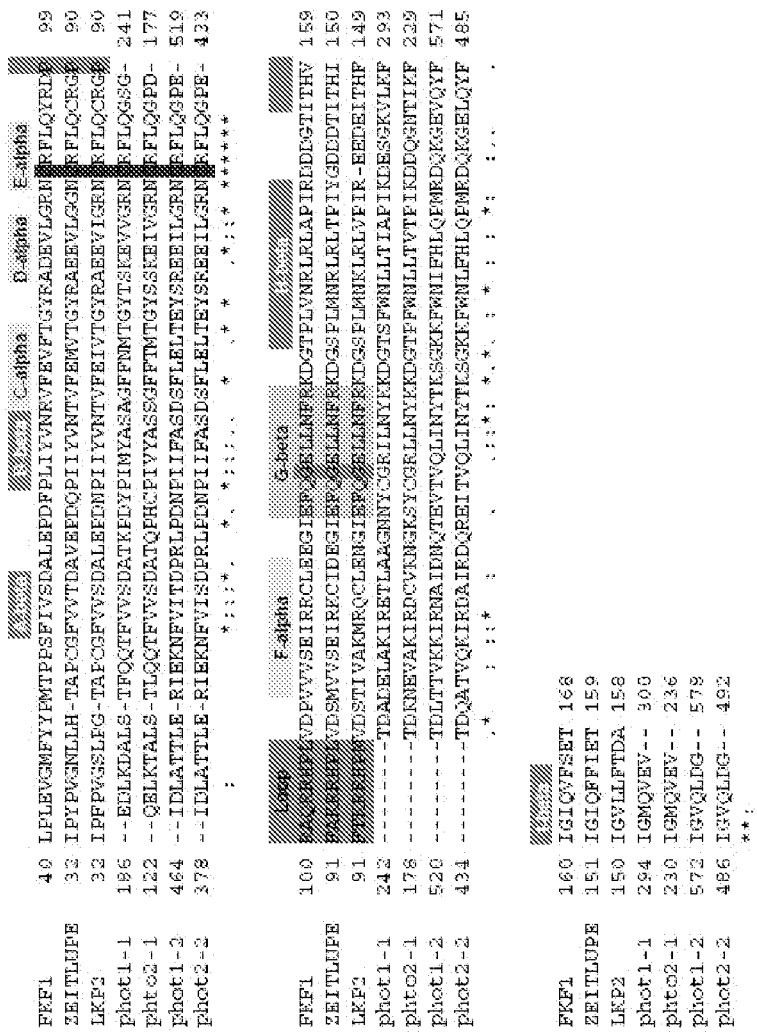
FIG. 7. Sequence alignment of LOV domains from FKF1 and phototropin family members The loop between E-alpha and F-alpha helixes that is specific to FKF1 family members is labeled "Loop" and shown in gry box. The Gbeta sheet that is completely conserved in the FKF1 family but not in phot1/2 LOV1/2 domains is labelled "G-beta" and shown in a grey box and the G128 residue that reduces basal interaction between FKF1 and GI is highlighted with a darker gray color within the grey box and below the label "G-beta".The C91 residue which is essential for the formation of the cysteinyl-flavin adduct and for detection of light is shown with a dark grey shading below the label "E-alpha". Phototropin1 LOV2 domain does not bind to GI.

High levels of basal interaction are undesirable in an inducible dimerization system, so we set out to engineer proteins with reduced light-independent binding. First, we used deletion analysis to map the interacting domains of FKF1 and GI, and found that both the LOV domain and the N-terminus of FKF1 upstream of this domain are necessary for interaction with GI (FIG. 6). Next we introduced a series of point mutations into these domains of FKF1, and measured the ability of the FKF1 mutants to interact with membrane-bound GI. The majority of the mutants that we generated had no effect on basal binding, but we identified six point mutations in the LOV domain and a six amino acid substitution in the N-terminus that reduced binding of FKF1 to GI (Table 1). One mutation, a substitution of glycine 128 for aspartate (G128D), completely prevented the recruitment of FKF1-YFP to GI-mCherry-CAAX to the cell surface (FIG. 2a, right panels). In contrast to the wild type (WT) FKF1-YFP, the interaction of the G128D FKF1 mutant with GI did not increase significantly with the concentration of either GI or FKF1, suggesting that this mutation reduces or eliminates FKF1-GI interaction in the absence of blue light (FIGS. 2a,b and c; red symbols). Analysis of the sequence of FKF1 revealed that the G128D mutation is in the Gβ sheet region of the FKF1 LOV domain; a region that is highly conserved in the FKF1 family members ZEITLUPE and LKP2 that are also thought to bind to GI, but not among other LOV containing proteins (FIG. 7).

TABLE 1

Effects of mutagenesis of FKF1 on basal binding to GI

| reduced basal binding | no effect |
|---|---|
| L120S[a] | P41A&V44A |
| L120D[a] | P54C&S55G |
| G128D[13] | P53S&P54C&S55A |
| G128A | R82S |
| E129A | L120Q |
| E129K | L120N |
| PMTPPS50-55VDTSCA[c] | E125Q |
| | Q127E |
| | Q127N |
| | Q127A |
| | E129Q |
| | E129S |
| | L131I |
| | L144F |
| | R145G |
| | D151A&D152A&D153A |
| | L214A[b] |
| | L214A&L227A[b] |
| | E217K[b] |

[a]No basal binding even at high levels of expression of FKF1 and GI
[b]Mutations disrupt function of Fbox[13]
[c]Mutations of six aa at position 50-55

We examined whether FKF1 with a G128D substitution could still interact with GI in response to blue light. Illumination of cells expressing both G128D FKF1-YFP and GI-mCherry-CAAX significantly increased the concentration of G128D FKF1-YFP at the cell membrane of almost all the cells over the course of thirty minutes (FIG. 2d). This interaction required a functional LOV domain, as a G128D FKF1-YFP containing a C91A mutation that prevents the formation of the cysteinyl-flavin adduct was not recruited to the membrane by illumination (FIGS. 2e and f). Interestingly, the amount of membrane recruitment in cells expressing G128D FKF1-YFP and cells expressing low levels of WT FKF1 was similar (FIG. 2f). The G128D mutation therefore increases the robustness of the FKF1-GI interaction by reducing the amount of light-independent binding of FKF1 to GI and reducing its dependence on protein concentration.

Figure 8:
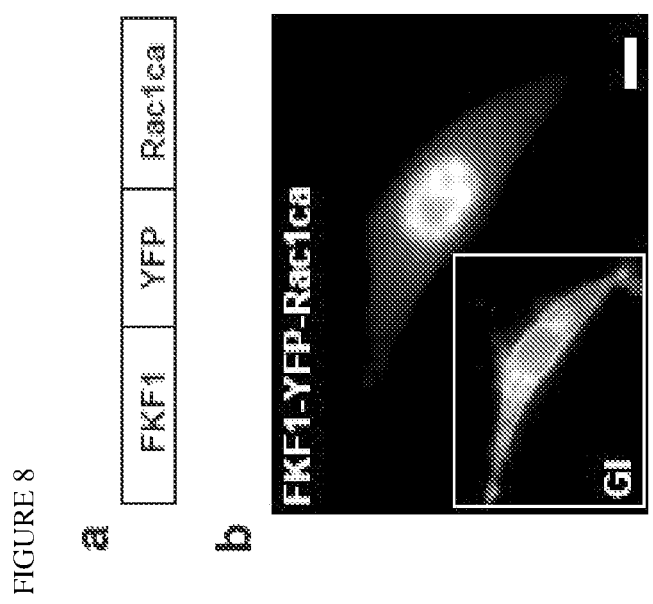
FIG. 8. Localization of FKF1-Rac1 fusion proteins a) Schematics of FKF1-YFP fused to a constitutively active Rac1 (FKF1-YFP-Rac1ca). b) Expression of FKF1-YFP-Rac1ca in NIH 3T3 cells along with GI-mCherry-CAAX (GI) shows significant nuclear localization in the absence of light. Scale bar=10 µm.

We next asked if the light-induced interaction of FKF1 and GI could be used to control a signaling cascade in mammalian cells. The small GTPase Rac1 is an important regulator of the cytoskeleton and plays a key role in controlling cellular morphology and movement by generating wavelike cellular extensions called lamellipodia. Rac1 activity requires GTP binding and recruitment to the plasma membrane by a C-terminal CAAX domain. To generate a Rac1 protein that could be controlled by light, we deleted the endogenous CAAX domain and introduced a G12V mutation that reduces the GTPase activity of the protein and keeps it bound to GTP. The absence of a CAAX domain means that even though this protein is bound to GTP, it does not localize to the cell membrane and therefore is not active. We fused the modified Rac1 to FKF1-YFP and added a linker to improve Rac1 function in cells (FIG. 3a) and a nuclear export sequence (NES) to prevent nuclear accumulation of Rac1 (FIGS. 8a and b).

Figure 3:
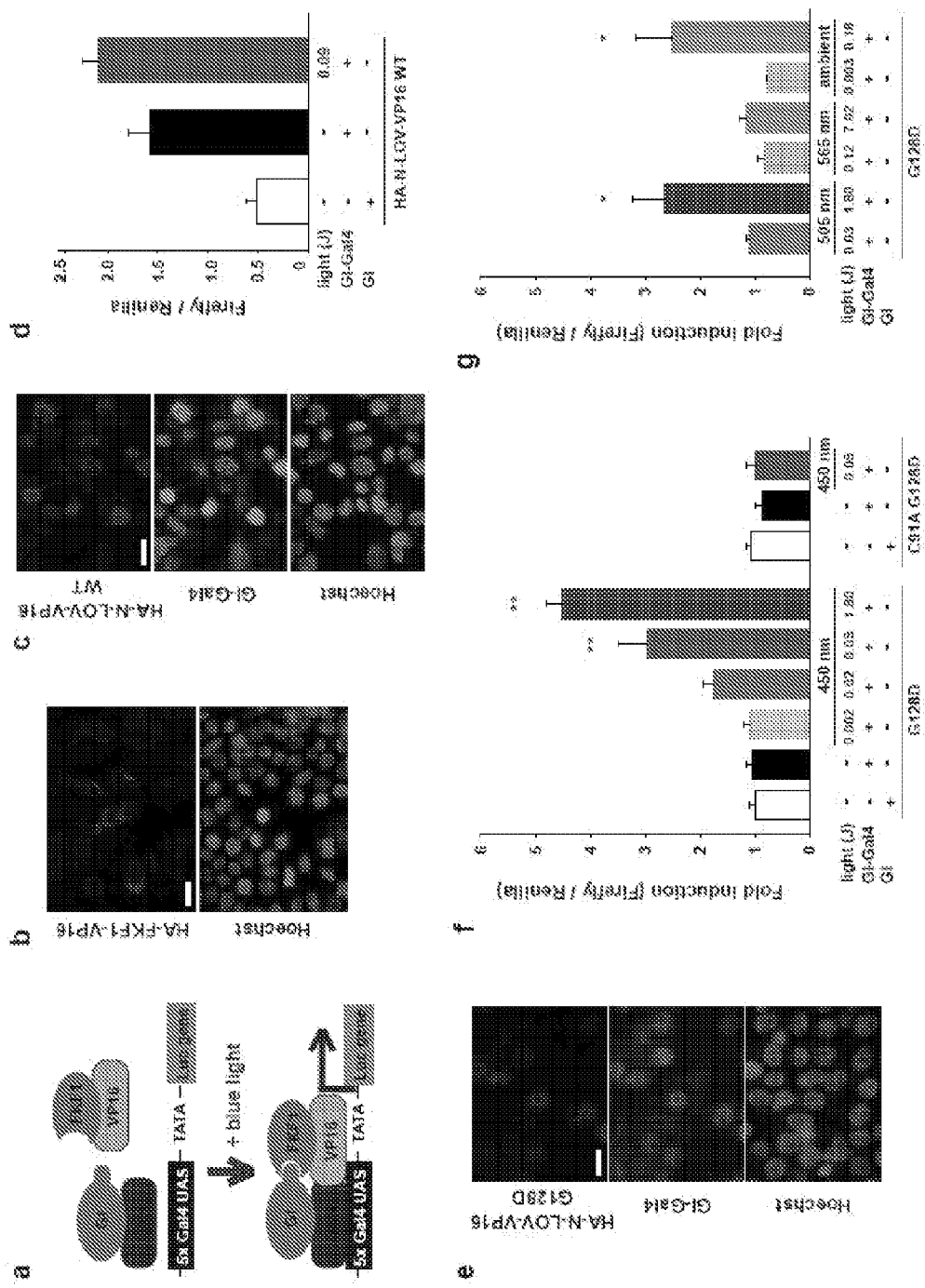
FIG. 3 Light-induced activation of transcription. a) Schematic representation of the GI-Gal4 and FKF1-VP16 fusion proteins used to control luciferase (Luc) gene expression with blue light. b) Immunocytochemistry of HEK 293T cells expressing HA-FKF1-VP16 using anti-HA antibodies to detect FKF1-VP16 and Hoechst 33285 to detect the nuclei. All scale bars=10 µm. c) Immunocytochemistry of cells expressing HA-N-LOV-VP16 and GI-Gal4 using anti-HA-tag antibodies to detect HA-N-LOV-VP16, anti-Gal4 to detect GI-Gal4 and Hoechst 33285 to detect the nuclei. d) Luciferase activity of cells expressing HA-N-LOV-VP16 along with GI (white) or GI-Gal4 before (black) or after (blue) illumination. The luciferase activity is shown as the ratio of Firefly to Renilla activity (mean±s.e.m. n=6, P<0.01.) e) Immunocytochemistry of cells expressing HA-N-LOV-VP16 G128D and GI-Gal4. f) Luciferase assay of cells expressing HA-N-LOV-VP16 G128D (left six columns) or HA-N-LOV-VP16 C91A G128D mutation (right three columns) and GI or GI-Gal4. Cells were illuminated with 5 mm diameter spot of light for 30 seconds, 5 minutes or 30 minutes to achieve 0.002, 0.02 J or 0.09 J of light energy or with a 2.4 cm spot of light for 30 minutes to achieve 1.8 J of energy (n=5-15 in G128D; n=5 in C91A G128D in at least two independent experiments; mean±s.e.m. P<0.01). g) Response of cells expressing LAD-Gal4 VP16 system to 30 second or 30 minute pulse of 505 nm, 565 nm or ambient light (n=3-4; mean±s.e.m. *P<0.05). Intensity of illumination is indicated.
Figure 9:
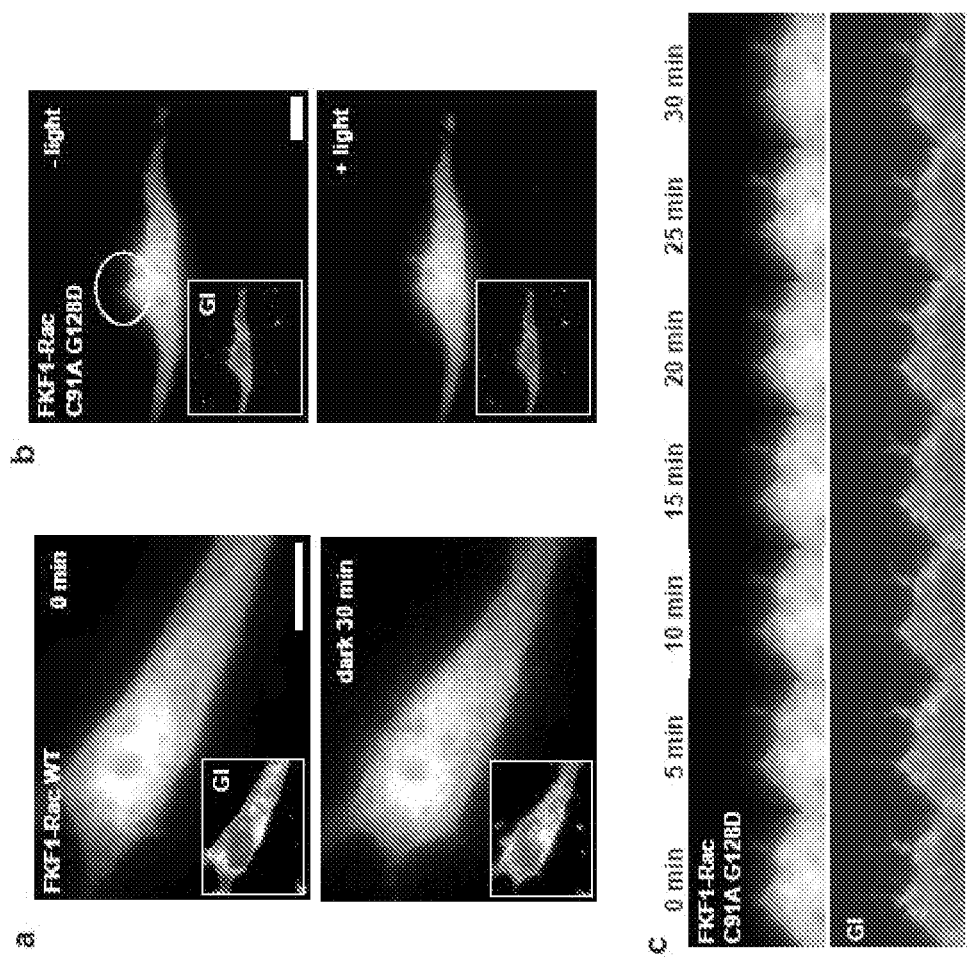
FIG. 9. Control experiments of FKF1-Rac1 fusion proteins a) Cell expressing FKF1-Rac WT and GI-mCherry-CAAX under dark condition. b) Cell expressing light insensitive FKF1-Rac C91A G128D mutant and GI-mCherry-CAAX before and after blue light exposure to limited region (white circle). c) Images of regions exposed to light in the cell expressing light insensitive FKF1-Rac C91A G128D mutant and GI-mCherry-CAAX. Scale bars=10 µm.

To test the ability of FKF1-Rac to induce lamellipodia in live cells in response to light, we transfected NIH 3T3 cells with FKF1-Rac and GI-mCherry-CAAX and imaged the cells using time-lapse fluorescence microscopy. Illumination of these cells with 450 nM light for five minutes led to the relocalization of FKF1-Rac from the cytoplasm to the cell membrane and a robust increase in the formation of lamellipodia over the course of thirty minutes (FIG. 3b and FIG. 9a). The percentage of cells with lamellipodia increased by 46% upon illumination of cells expressing WT FKF1-Rac, and by 87% in cells expressing FKF1-Rac containing the G128D mutation. In contrast, there was no change in the number of lamellipodia in cells expressing FKF1-YFP not fused to Rac1 (FIG. 3e) or in cells expressing FKF1-Rac with a C91A mutation that disables the LOV domain (FIG. 8c). Similarly there was no significant change in FKF1-Rac localization or in lamellipodia formation in the absence of blue light (FIG. 3d and FIG. 9b) or in cells lacking GI. Examination of the lamellipodia using anti-GFP antibodies and phalloidin staining revealed increased concentrations of FKF1-Rac and oligomerized actin at the sites of lamellipodia formation (FIG. 3c) indicating that Rac1 recruitment led an increase in actin oligomerization. Taken together, these data show that the PICL system can be used to activate a signaling cascade and to alter the morphology of mammalian cells in response to blue light.

We next sought to determine whether we could use PICL to induce lamellipodia in specific subcellular regions using focused light. We illuminated cells expressing GI-mCherry-CAAX and FKF1-Rac1 with a 2 μm diameter spot of light that was focused on a region of the cell membrane, and monitored cell growth using time-lapse microscopy. We found that cells extended lamellipodia-like projections in the region that was illuminated (FIGS. 3f and g top panel), but not in neighboring regions that were not illuminated (FIG. 3g bottom panels). Membrane extension was observed in most of the illuminated regions but was most pronounced in growth cones. Focal illumination did not trigger growth of lamellipodia in cells expressing FKF1-Rac C91A, suggesting that the projection of the cell membrane depends on the light-inducible interaction of FKF1-Rac and G1-mCherry-CAAX (FIGS. 9b and c). These results indicate that PICL can be used to activate signaling cascades locally and investigate the effects of these manipulations on cellular morphology.

Figure 4:
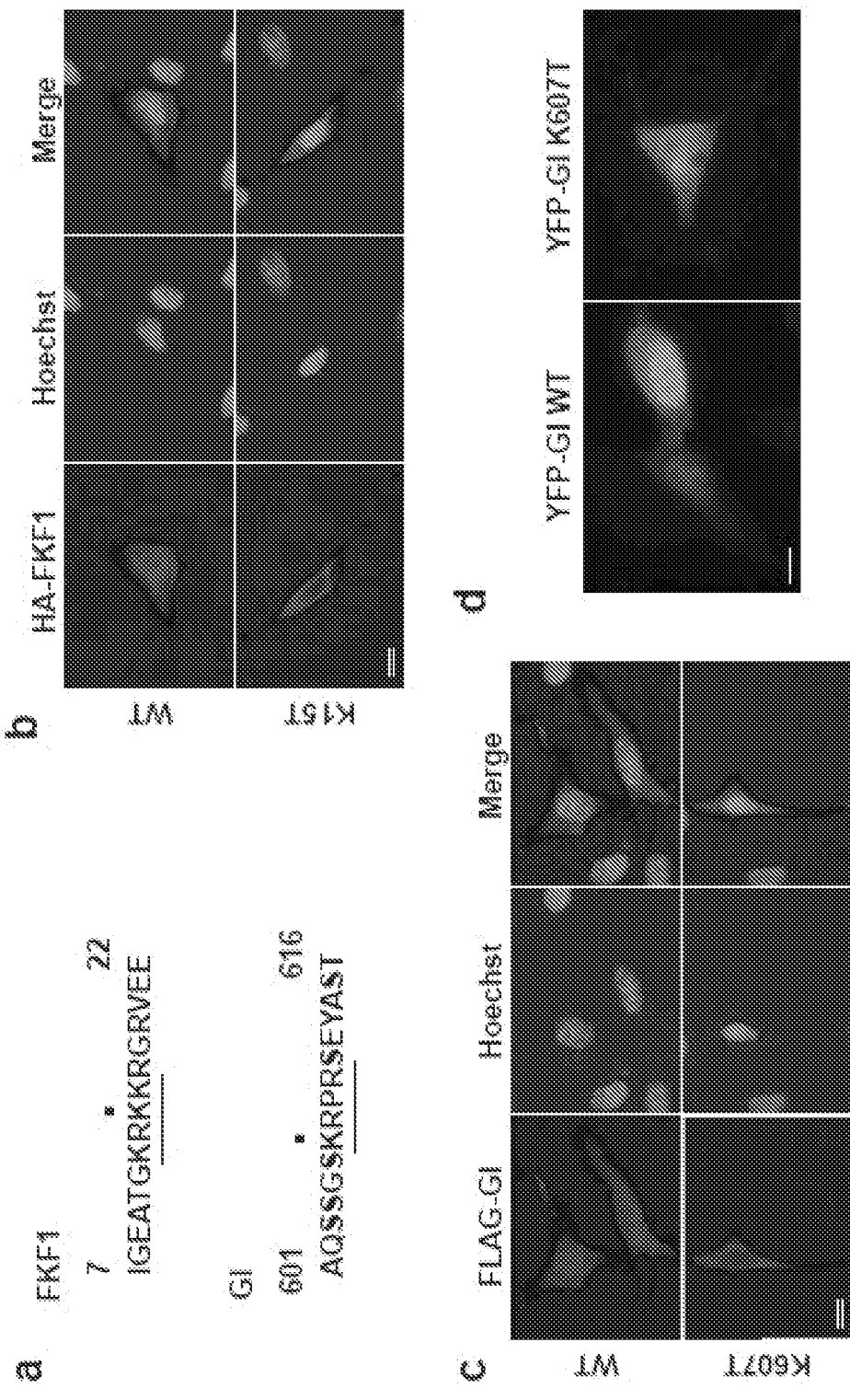
FIG. 4. Localization of FKF1 and GI with a mutation of the putative nuclear localization signal a) Amino acid sequences of putative nuclear localization signals (underlined) in FKF1 and GI. Dots show the lysines that were mutagenized to threonine to eliminate nuclear trafficking. b) Anti HA staining of NIH 3T3 cells expressing either HA-tagged WT or K15T FKF1. HA antibody staining is shown in the column designated "HA-FKF1"and Hoechst 33285 staining of nuclei in is shown in the column labeled "Hoechst". c) Anti-FLAG antibody staining of NIH 3T3 cells expressing either FLAG tagged WT or K607T GI. d) NIH 3T3 cells expressing YFP-GI WT or the K607T mutant. Fusion of YFP to the GI-K607T mutant increases nuclear expression relative to FLAG-GI K607T shown in (c). Scale bars=10 µm.

As a second example of the utility of PICL in regulating cellular signaling, we developed a light-regulated transcriptional activation system. The yeast transcription factor, Gal4, is widely used to regulate the expression of ectopic genes driven by the UAS promoter in flies, rodents and other organisms. A light-activated version of Gal4 would allow us to regulate gene expression in single cells at specific points in development. The DNA binding domain of the yeast transcription factor Gal4 binds autonomously to the UAS sequence but does not activate transcription in the absence of a transactivation domain. VP16 is a potent transactivation domain that acts by recruiting basal transcription factors to the promoter/enhancer of a gene, but it does not act in the absence of a DNA binding domain. To generate a light-inducible transcription factor, we fused GI containing an intact NLS to the DNA binding domain of Gal4, and we fused FKF1 to VP16 (FIG. 4a).

Figure 10:
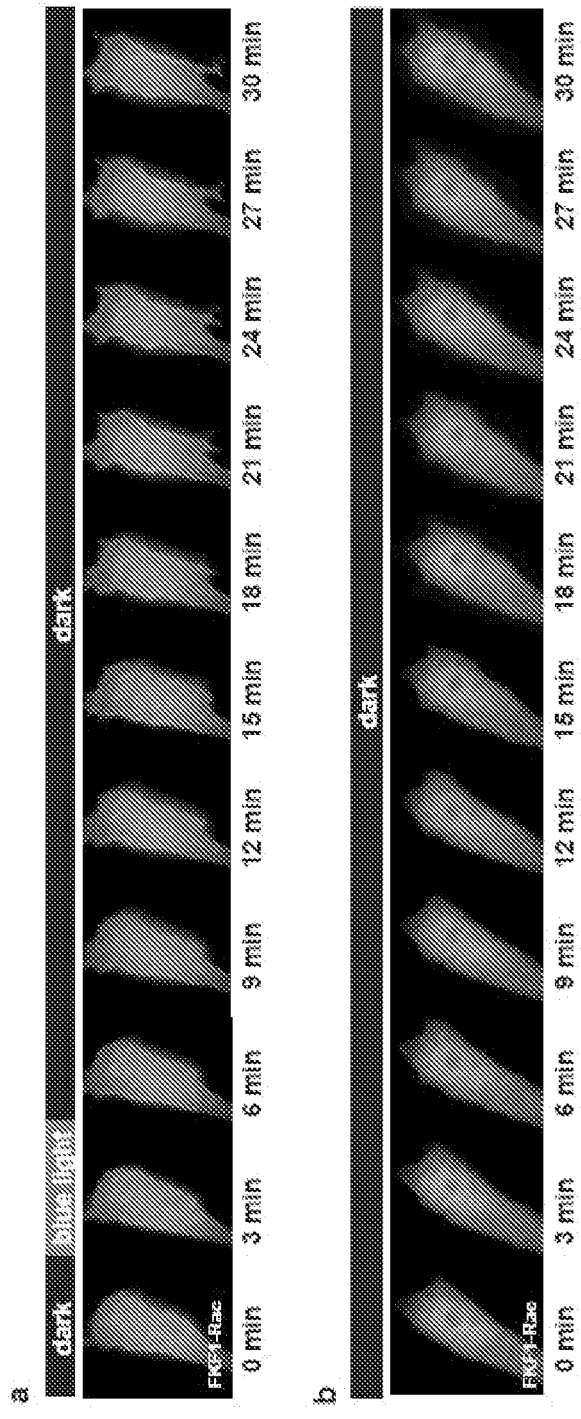
FIG. 10. Light-induced recruitment of FKF1-Rac to the plasma membrane and formation of lamellipodia a) NIH 3T3 cell images expressing FKF1-Rac and GI-mCherry-CAAX before and 25 minutes after a 5 minute exposure to blue light. b) Cell images expressing FKF1-Rac and GI-mCherry-CAAX in the dark.
Figure 11:
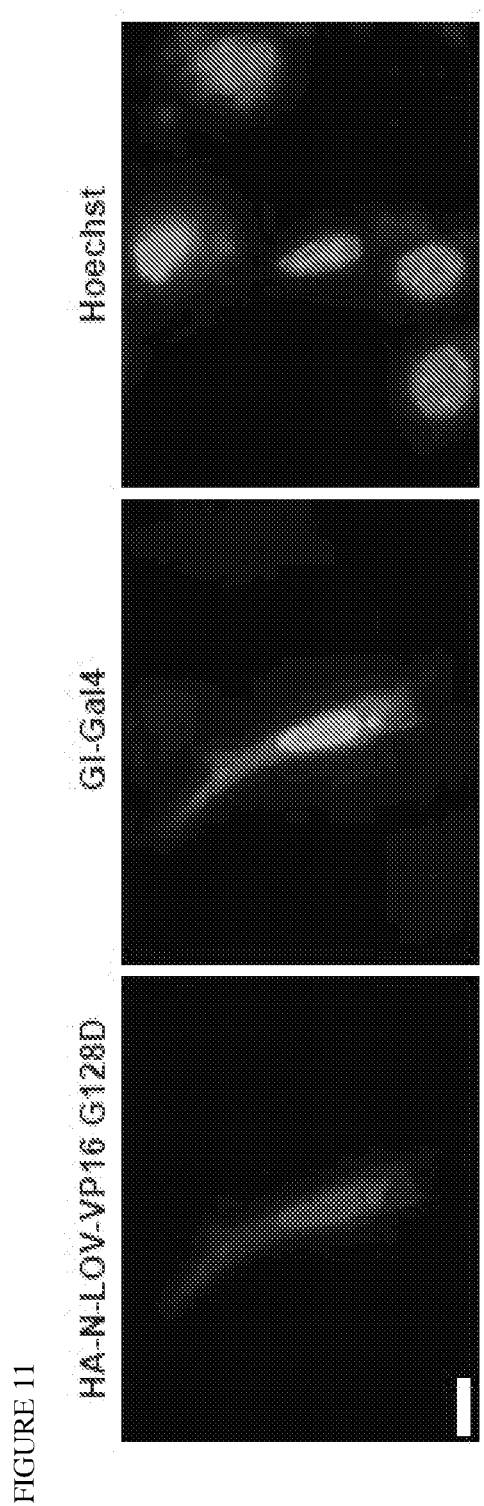
FIG. 11. Nuclear localization of HA-N-LOV G128D fused to VP16 Immunocytochemistry of NIH 3T3 cells expressing HA-N-LOV-VP16 G128D and GI-Gal4. HA-N-LOV-VP16 G128D was detected with ant-HA antibodies, GI-Gal4 with anti-Gal4 antibodies and nuclei with Hoechst 33285. Scale bar=10 µm.

Surprisingly, FKF1-VP16 was expressed largely in the cytoplasm of 293T cells (FIG. 4b), where it was unlikely to encounter GI-Gal4. We therefore took advantage of the observation that FKF1 lacking the C-terminus but containing the LOV domain (N-LOV) was expressed in the nucleus (FIG. 6a). We fused the N-LOV to VP16, introduced it into 293T cells along with GI-Gal4, and measured its expression and ability to activate transcription using a UAS-luciferase reporter gene. Both N-LOV-VP16 and GI-Gal4 were expressed at high levels in the nucleus of 293T cells (FIG. 4c). In the absence of light these cells had elevated levels of luciferase, consistent with our earlier finding that the WT N-LOV domain has increased affinity for GI (FIG. 4d and FIG. 6a). In contrast, an N-LOV-VP16 containing a G128D mutation was well expressed in the nucleus of cells (FIG. 4e and FIG. 10), and resting cells had low levels of luciferase similar to those observed in cells expressing N-LOV-VP16 and GI without Gal4. Upon illumination, we observed a significant increase in luciferase production that was proportional to the duration of exposure to light (FIG. 4f). Thirty seconds, five minutes, and thirty minutes of blue light illumination led to 22%, 130% and 280% increases in the amount of transcription, respectively. These experiments provide evidence that PICL can be used effectively to control the activation of transcription in response to blue light in mammalian cells.

The present invention provides a set of tools for controlling the activity of proteins, such as Rac1 and Gal4, that are immediately useful to the biological community. Rac1 is a key initiator of a wide variety of biological events including dendritic spine formation in neurons, B and T cell development and cardiac growth and hypertrophy. The PICL Rac1 will be extremely useful for controlling dendritic spines formation with temporal and spatial precision, for regulating immune development and for controlling cardiovascular function in live animals. We have also developed a light-activated transcription factor based on the widely-used Gal4-VP16 system. The PICL Gal4 system allows the use of light to activate the expression of a gene in single cells, for example in an animal such as *Drosophila* in which a large number of UAS-driven lines have been established. It is also useful in mammals where other light regulated transcription factors, such as those based on Phytochrome B and Phytochrome interaction factor3 (PIF3), work poorly.

PICL has several advantages relative to existing methods for controlling protein-protein interactions using small organic molecules such as FK1012, rapamycin, and coumermycin. First, because flavin-mononucleotide, the FKF1 chromophore, is widely available inside cells, our system does not require introduction of an exogenous agent. Second, unlike soluble molecules that must be administered systemically to animals or applied to cells in a bath, light can be delivered with great spatial and temporal precision allowing selective control of protein interactions in single cells or in subcellular domains. Third, exposure with dim blue light such as is required to activate PICL produces relatively little toxicity and has few off-target effects in most cells, while small molecules have endogenous targets and numerous side effects. The possibility of light-induced toxicity is further decreased in the PICL system by the interesting finding that the interaction between FKF1 and GI reverses slowly. This means that a protein interaction induced by blue light remain stable for hours, reducing the need for continuous exposure of cells to blue light. Finally, the PICL system is comparatively simple to use in intact organisms like flies and worms and only requires equipment such as microscopes and lamps that are widely available in biological laboratories.

Importantly, the PICL system greatly expands the range of cellular events that can be controlled using light in cells. Adapting the technology to the small G protein Rac1 and the transcription factor Gal4 required very little optimization, demonstrating that this system is easily transferable and can be applied to study any signaling system that requires protein-protein interactions. For instance, PICL constructs can confer light-dependent regulation to any transcription factor for which a DNA binding domain can be identified. The formation of specialized cellular structures like synapses can be induced at particular locations by creating PICL fusions of synaptic proteins and using focused light to induce their interaction. Finally, by fusing PICL tags to the cytoplasmic domains of receptor tyrosine kinases, it should be possible to use light to activate specific receptors using light. The tools described in this paper should thus be widely applicable for many studies of cellular and organismal biology, and will greatly extend the uses of light to control biochemical pathways.

Methods:

Cell culture: NIH 3T3 and HEK 293T cells were cultured in Dulbecco's Modified Eagle Media (DMEM, Invitrogen #10313021) supplemented with 10% fetal bovine serum, 2 mM L-glutamine, 100 unit/ml penicillin and 100 μg/ml of streptomycin. NIH 3T3 and HEK 293T cells were passaged using 0.25% trypsin+0.03% EDTA solution (GIBCO) and 0.05% trypsin+0.03% EDTA solution (GIBCO), respectively.

Plasmid construction: DNA constructs were generated using conventional restriction and ligation methods and PCR using Pfu turbo polymerase (Stratagene). Site directed mutagenesis was done using QuickChange Site Directed Mutagenesis Kit (Stratagene) according to the manufacturer's instructions. Briefly, HA-FKF1 was constructed by the insertion of HA-FKF1 sequence obtained from pCR-Blunt II-HA-FKF1 (from Dr. Imaizumi) with NotI/SpeI digestion into NotI/XbaI sites in pcDNA3 vector (Invitrogen) and then by removing the sequence between two EcoRV sites. The plasmid encoding FLAG-GI was generated by Gateway technology (Invitrogen) with pENTR/D-GI from Dr. Imaizumi and a destination vector called pDEST-GW1-FLAG that contains a cytomegalovirus (CMV) promoter and an N-terminal FLAG-tag in frame with the attR acceptor sequences. GI-mCherry-CAAX was constructed first by the insertion of an annealed CAAX oligo (F: GGCCGCAcataaagaaaagatgag-caaagatggtaaaaagaagaaaaa-gaagtcaaagacaaagtgtgtaattatgtaaT, R: CTAGAttacataattaca-cactttgtctttgacttcttttcttcttttaccatctttgctcatcttttctttatgTGC) into NotI/XbaI sites in pcDNA3 and then by inserting PCR amplified fragments of GI and mCherry into EcoRI/NotI sites of the pcDNA3 vector containing CAAX sequence. FKF1-YFP was constructed by the insertion of PCR amplified portions of FKF1 and YFP into the pcDNA3 vector. NES-FKF1-YFP-linker-Rac1 was constructed first by the insertion of a PCR amplified portion of human Rac1 G12V mutant from Dr. Gotoh into NotI/XbaI sites of pcDNA3 vector and then by inserting an annealed linker oligo containing additional EcoRI sites (F: gatcctgaattcAGTGCTGGGAGTGCTG-GCAGTGCTGGAAGTGCTGGTAGTGCTGGcgc, R: ggc-cgcgCCAGCACTACCAGCACTTCCAG-CACTGCCAGCACTCCCAGCACTgaattcag) into BamHI/NotI sites of the plasmid containing Rac1 mutant, and finally by inserting a PCR amplified fragment of FKF1-YFP into BamHI/EcoRI sites into the vector containing linker and Rac1 sequences after removing BamHI and EcoRI sites in FKF1 sequence using sequential mutagenesis with two sets of primers as described below. HA-FKF1-VP16 and HA-N-LOV-VP16 were constructed by inserting a PCR amplified portion of either HA-FKF1 or HA-N-LOV with a VP16 PCR fragment derived from pTet-On Advanced plasmid (Clontech) into BamHI/NotI sites of pcDNA3. The plasmid encoding GI-Gal4 was generated by the insertion of PCR amplified fragments of GI and Gal4 DNA binding domain from pFA-CMV (Stratagene) into EcoRI/XbaI sites of pcDNA3 vector. The primers used for the mutagenesis are shown below:

```
FKF1 K15T
F: GAAGCCACCGGAAAACGAAcGAAACGCGGCAGAGTTGAAG

R: CTTCAACTCTGCCGCGTTTCgTTCGTTTTCCGGTGGCTTC

GI K607T
F: GCACAGTCTAGTGGTAGCAcGAGACCGAGAAGTGAATATGC

R: GCATATTCACTTCTCGGTCTCgTGCTACCACTAGACTGTGC

FKF1 G128D
F: GAAGAAGGTATTGAATTCCAAGacGAGCTTCTTAATTTCAGAAAAG
ATGG

R: CCATCTTTTCTGAAATTAAGAAGCTCgtCTTGGAATTCAATACCTT
CTTC

FKF1 C91A
F: CGATGAAGTTCTTGGTCGTAACgcTCGATTCCTACAGTACAGAGATC

FKF1 w/o EcoRI
F: GGAGATGTCTTGAAGAAGGTATTGAgTTCCAAGGAGAGCTTCTTAA
TTTCAG

R: CTGAAATTAAGAAGCTCTCCTTGGAAcTCAATACCTTCTTCAAGAC
ATCTCC

FKF1 w/o BamHI
F: CAGAAGAGAAACCGTCATGGAgAATCCTGAATGTCCCCGGGAAAC

R: GTTTCCCGGGGACATTCAGGATtCTCCATGACGGTTTCTCTTCTG
```

FKF1 and GI Constructs

| name | purpose | feature |
|---|---|---|
| HA-FKF1 WT | characterization of FKF1 localization | localized in nucleus and cytoplasm |
| HA-FKF1 K15T | characterization of FKF1 localization | localized in cytoplasm |
| FKF1 (K15T)-VFP WT | light-induced translocation to plasma membrane (PM) | can be translocated to PM with light |
| FKF1 (K15T)-YFP G128D | light-induced translocation to PM | can be translocated to PM with light, less basal binding to GI |
| FKF1 (K15T)-YFP C91A&G128D | light-induced translocation to PM | a light-insensitive mutant |

| name | purpose | feature |
|---|---|---|
| FKF1 (K15T)-VFP-Rac-tca | light-induced Rac1 translocation to PM | localized in nucleus, less efficiency to induce lamellipodia |
| NES-FKF1(K15T)-YFP-linker-Rac1ca(FKF1-Rac) | | |
| WT | light-induced Rac1 translocation to PM | localized in cytoplasm mainly, can induce lamellipodia |
| G128D | light-induced Rac1 translocation to PM | localized in cytoplasm mainly, can induce lamellipodia |
| C91A&G128D | light-induced Rac1 translocation to PM | a light-sensitive mutant |
| HA-FKF1-VP18 | light-induced activation of transcription | localized in cytoplasm |
| HA-N-LOV-VP18 WT | light-induced activation of transcription | localized in nucleus, higher basal binding to GI |
| HA-N-LOV-VP18 G128D | light-induced activation of transcription | localized in nucleus, less basal binding to GI, can activate transcription with light |
| HA-N-LOV-VP18 C91A&G128D | light-induced activation of transcription | a light-insensitive mutant |
| N-LOV (K15T)-YFP | characterization of FKF1 binding to GI | localized in nucleus, higher basal binding to GI |
| LOV-mCherry-CAAX | characterization of FKF1 binding to GI | localized in PM, no binding to YFP-GI K607T |
| G-beta-mCherry-CAAX | characterization of FKF1 binding to GI | localized in PM, no binding to YFP-GI K607T |
| Loop-mCherry-CAAX | characterization of FKF1 binding to GI | localized in PM, no binding to YFP-GI K607T |
| FLAG-GI WT | characterization of GI localization | localized in nucleus and cytoplasm |
| FLAG-GI K607T | characterization of GI localization | localized in cytoplasm |
| GI (K607T)-mCherry-CAAX | light-induced translocation to PM | localized in PM |
| GI (K607T)-CAAX | light-induced Rac1 translocation to PM | localized in PM, without mCherry for phalloidin-TRITC staining |
| GI-Gal4 | light-induced activation of transcription | localized in nucleus |
| GI | light-induced activation of transcription | a negative control in light-induced activation of transcription |
| YFP-GI WT | characterization of FKF1 binding to GI | localized in nucleus mainly |
| YFP-GI K867T | characterization of FKF1 binding to GI | localized in cytoplasm and nucleus |

Cell transfection: Cells were plated on 18 mm coverslips (Fisher Scientific) placed in 24-well plates or in 8-well chamber slides (Lab-Tek II, Nalgen Nunc International) that were coated with 20 µg/ml of poly-ornithine (Sigma Aldrich) at 37° C. for ~30 min and then washed twice with PBS. NIH 3T3 cells were plated at $5 \times 10^4$ cell/ml on 24 well plates (0.5 ml/well) or on 8 chamber slides (0.25 ml/well) and then were transfected using Lipofectamine (Invitrogen) at a ratio of 0.8 µg of DNA to 2.0 µl of lipofectamine in 100 µl of OptiMEM (Invitrogen) for a well of a 24-well plate. GI and FKF1 constructs were transfected at a 3:1 ratio. All manipulations of FKF1 and GI expressing cells were carried out either in the dark or using dim red light.

Cell staining and imaging: Twenty to thirty hours after transfection, the cells were either fixed and processed for immunocytochemistry or placed in a chamber and mounted on the stage of an inverted microscope for live cell imaging. Immunocytochemistry was carried out using standard protocols with antibodies against HA-tag (3F10 Roche; 1:1,000), FLAG-tag (M2 Sigma Aldrich; 1:1,000) and Gal4 DNA binding domain (RK5C1 Santa Cruz Biotechnology; 1:400) with Hoechst33285 (Molecular Probes; 1:10,000). For live imaging experiments, the tissue culture media was exchanged for Tyrodes solution (129 mM NaCl, 5 mM KCl, 2 mM $CaCl_2$, 1 mM $MgCl_2$, 30 mM glucose and 25 mM HEPES; pH 7.4 adjusted with NaOH). Live cell imaging was conducted at 37° C. with using 40× (NA 1.42) or 100× (NA 1.49) lens oil immersion objectives (Nikon) on the stage of a Nikon Eclipse TE2000U inverted microscope. The microscope was equipped with a lambda LS Xenon Arc lamp (Sutter Instruments), filter cubes optimized for either YFP, CFP or RFP (Chroma Technology), an ORCA-ER camera from Hamamatsu. The microscope was controlled using a computer running Openlab software from Perkin Elmer. The camera setting for the majority of experiments was for 500 ms exposure, 124 gain and 1× binning. 450 nm (blue light) stimulation of cells was achieved using the CFP filter cube, and the lamp was attenuated ten fold with a neutral density filter.

Analysis of plasma membrane population: Using ImageJ software (NIH), images of NIH 3T3 cells expressing both FKF1-YFP and GI-mCherry-CAAX proteins were analyzed. First, the region of plasma membrane in cells was determined by plot profiling of plasma-membrane localized GI-mCherry-CAAX intensity in cell images, and then the fraction of plasma-membrane localized FKF1-YFP intensity was divided by fraction of whole FKF1-YFP intensity in the cell images to calculate plasma membrane population of FKF1-YFP proteins.

Lamellipodia assay: Twenty four hours after transfection, NIH 3T3 cells were incubated in serum-free DMEM media for 6 hr in the dark before illumination with blue light and live cell imaging. Live cell imaging was conducted at 37° C. in Tyrodes solution. Fluorescent images for the movies were taken once per min to minimize photodamage. For phalloidin staining, the cells were exposed to blue light for 5 min and placed in the incubator in the dark for two hours before fixation with 4% paraformaldehyde (EM grade, Electron Microscope Science) and 2% sucrose in PBS for 15 min at room temperature. Cells were washed with PBS followed by blocking and permeabilization using 0.25% Triton X-100 and 3% BSA in PBS at room temperature for 30 min. The cells were then incubated with rabbit anti-GFP polyclonal antibody (MBL; 1:1,000) for 1 hr at room temperature to detect the expression of NES-FKF1-YFP-linker-Rac1. Following a second wash in PBS the cells were incubated with PBS containing phalloidin-TRITC (10 µg/ml, Sigma Aldrich) and antrabbit IgG Alexa Fluor 488 (2 µg/ml, Molecular Probes) for 30 min at room temperature, washed with PBS six times (6×5 min), stained with Hoechst33285 and mounted on slides (Becton, Dickinson and Company, Gold Seal Rite-On, #3050) using Aqua Poly/Mount (Polysciences).

Luciferase assays: HEK 293T cells were plated at $1.5 \times 10^5$ cell/well in 24-well plates coated with poly-ornithine and transfected the next day with 0.8 μg of DNA in 2 μl of Lipofectamine-2000 (Invitrogen) in 100 μl of OptiMEM. The ratio of FKF:GI:UAS-Luc:Renilla-Luc was as follows: 1:3:1:0.01. Twenty four hours after transfection, the cells were exposed to blue light for 30 sec, 5 min or 30 min at 37° C. and luciferase levels were assayed 24 hours later using the Promega Dual Luciferase Kit or a home made substitute and a Veritas 96 well luminometer (Turner biosystems) according to the instructions of the manufacturer. The luminescence of each sample was measured by integrating for 2 seconds after injection of the luciferase substrate.

Statistical Analysis: The statistical significance (P value) used to compare the samples with/without light exposure was determined using a Student's t-test (Excel, Microsoft). Spearman's correlation coefficient by rank test and simple regression test (Statcel, OMS and Excel, Microsoft) were used in FIGS. 2b and c. The statistical significance of the comparison of multiple samples for the luciferase assay was computed using the Bartlett test and one-factor ANOVA with a Bonferroni/Dunn test (FIG. 4d) and with Bartlett test, Kruskal-Wallis test and Scheffe's F test (FIG. 4f; Statcel, OMS and Excel, Microsoft).

What is claimed is:

1. A genetic construct comprising an expression vector encoding an L polypeptide having an interacting domain that specifically interacts with an I polypeptide upon light activation wherein said L-polypeptide consists of the amino acid sequence of SEQ ID NO:3 with one amino acid modification selected from the group consisting of G128D and G128E which reduces basal levels of interaction with the I polypeptide without substantially reducing light induced interaction with the I polypeptide.

2. The genetic construct of claim 1, wherein said coding sequence of said L polypeptide is fused to a coding sequence for a cellular protein of interest.

3. The genetic construct of claim 1, wherein said coding sequence of said L polypeptide further comprises a localization signal or a detectable label.

4. A kit for light-controlled protein interactions, the kit comprising:
    a genetic construct as set forth in claim 1; and a genetic construct comprising an expression vector encoding an I polypeptide which comprises the interacting domain sequence set forth in SEQ ID NO:6.

5. The kit of claim 4, wherein said genetic constructs comprise a cloning site for insertion of a cellular protein coding sequence.

6. A method for light controlled protein interaction in a cell comprising:
    introducing into said cell the genetic construct comprising the expression vector of claim 1 which encodes the modified L polypeptide consisting of the amino acid sequence of SEQ ID NO:3 which comprises one amino acid modification selected from the group consisting of G128D and G128E and a genetic construct comprising an expression vextor encoding an I polypeptide that specifically interacts with the L polypeptide upon light activation, and wherein one or both of said L polypeptide and said I polypeptide are fused to a cellular protein of interest;
    allowing said cell to express said L-polypeptide and said I polypeptide; and
    illuminating said cell with light at a wavelength that activates said interaction, thereby introducing the interaction of said L polypeptide with said I polypeptide.

7. The method of claim 6, wherein said I polypeptide is a modified GI protein.

8. The method of claim 7, wherein said I polypeptide consists of the interacting domain set forth in SEQ ID NO:6.

9. The method of claim 8, wherein one or both of said L polypeptide and said I polypeptides further comprises a cellular localization signal.

10. The method of claim 9, wherein said cellular localization signal is a membrane localization signal.

11. The method of claim 8, wherein one or both of said L polypeptide and said I polypeptides further comprise a detectable marker.

12. The method of claim 11, wherein said detectable marker is a fluorescent or bioluminescent polypeptide.

13. The method of claim 6, wherein said I polypeptide and said L polypeptide are independently fused to a transcription factor and a transactivation domain.

14. The method of claim 6, wherein said I polypeptide and said L polypeptide are independently fused to interacting cellular proteins.

15. The method of claim 14, wherein said cellular proteins are synaptic proteins.

16. The method of claim 6, wherein said I polypeptide or said L polypeptide is fused to a cellular receptor protein.

17. The method of claim 16, wherein said cellular receptor protein is a tyrosine kinase.

* * * * *

SEQUENCE LISTING

```
<160> NUMBER OF SEQ ID NOS: 6

<210> SEQ ID NO 1
<211> LENGTH: 1860
<212> TYPE: DNA
<213> ORGANISM: Arabidopsis thaliana

<400> SEQUENCE: 1
atggcgagag aacatgcgat cggagaagcc accggaaaac gaaagaaacg cggcagagtt      60
gaagaagcag aagaatactg taacgatgga atcgaagaac aagtagagga tgagaagctt     120
ccgttagagg ttgggatgtt ctattaccca atgactccgc cttcgttcat tgtttccgat     180
gctctggagc cagattttcc tttgatctat gtcaacagag tcttcgaagt cttcactggc     240
tatcgtgccg atgaagttct tggtcgtaac tgtcgattcc tacagtacag agatcctcga     300
gctcaaaggc gtcacccatt ggttgatcct gtggttgtat ctgagattag agatgtctt     360 gaagaaggta ttgaattcca aggagagctt cttaatttca gaaaagatgg tactcctttg     420
gttaacagac tacggcttgc tccaatacgt gacgatgatg gaaccattac acacgtaatt     480
gggatacagg tcttctctga aacgactata gaccttgacc gtgtctcgta tcctgtgttc     540
aaacataaac aacagcttga tcaaacatct gagtgcttgt ttccaagtgg aagcccgagg     600
tttaaggagc atcatgaaga tttctgtggg atattgcagc tatctgatga agttttggct     660
cataacatct tatctcggtt aactccaagg gacgttgctt caattggttc tgcttgcagg     720
aggttgaggc agttgacgaa gaacgagagt gtgaggaaga tggtatgtca gaatgcgtgg     780
ggaaaagaga taactggaac actggagatt atgactaaga agctaagatg gggtcggtta     840
gctagagagc tcaccactct tgaagctgtg tgttggcgta aatttactgt tggagggatt     900
gtacaacctt cccgctgcaa tttcagcgcg tgtgctgttg ggaaccggct tgtgctattt     960
ggtggggaag gggttaacat gcagccattg gatgatactt ttgttctcaa tcttgatgca    1020
gagtgtcctg agtggcagcg tgtgagggtg acgtcgtcgc ctccaggacg ttggggacac    1080
acactctcgt gtctcaacgg gtcgtggttg gtagtctttg gagggtgtgg aagacaagga    1140
ttgcttaatg atgtatttgt gcttgatcta gacgctaagc atcccacatg gaaggaagta    1200
gcaggaggaa ctcctccatt gccaagatct tggcacagct cgtgcaccat tgagggctct    1260
aaactggttg tctcaggtgg ctgcacagac gctggagtgc ttctcagcga caccttcttg    1320
ttggatctga aacagataa accgacatgg aaagagatcc cgacatcatg ggctcctcct    1380
tctagacttg ggcattcttt atcggtcttt ggtcggacta aaatcctaat gtttggcggg    1440
cttgcaaata ttggtcatct aaagctaagg tcaggggagg catacactat agacttggag    1500
gatgaagaac caagatggag agagcttgag tgtagcgcat tcccaggcgt ggttgtaccg    1560
cctccaagac tagaccatgt ggctgtgagc atgccgtgtg gtagggtcat catctttgga    1620
```

```
gggtcgattg cagggcttca ctctccttcg caactgtttc taatagatcc tgcagaagag    1680
aaaccgtcat ggaggatcct gaatgtcccc gggaaaccgc ctaagttagc ttggggacat    1740
agcacatgcg ttgttggagg aactagagta ttggtccttg gtggtcacac tggtgaggaa    1800
tggatactca atgaattaca tgaactctgc ttggctagcc ggcaagactc ggatctgtaa    1860
```

<210> SEQ ID NO 2
<211> LENGTH: 619
<212> TYPE: PRT
<213> ORGANISM: Arabidopsis thaliana

<400> SEQUENCE: 2

```
Met Ala Arg Glu His Ala Ile Gly Glu Ala Thr Gly Lys Arg Lys Lys
 1               5                  10                  15

Arg Gly Arg Val Glu Glu Ala Glu Glu Tyr Cys Asn Asp Gly Ile Glu
                20                  25                  30

Glu Gln Val Glu Asp Glu Lys Leu Pro Leu Glu Val Gly Met Phe Tyr
            35                  40                  45

Tyr Pro Met Thr Pro Pro Ser Phe Ile Val Ser Asp Ala Leu Glu Pro
        50                  55                  60

Asp Phe Pro Leu Ile Tyr Val Asn Arg Val Phe Glu Val Phe Thr Gly
65                  70                  75                  80

Tyr Arg Ala Asp Glu Val Leu Gly Arg Asn Cys Arg Phe Leu Gln Tyr
                85                  90                  95

Arg Asp Pro Arg Ala Gln Arg Arg His Pro Leu Val Asp Pro Val Val
                100                 105                 110

Val Ser Glu Ile Arg Arg Cys Leu Glu Glu Gly Ile Glu Phe Gln Gly
            115                 120                 125

Glu Leu Leu Asn Phe Arg Lys Asp Gly Thr Pro Leu Val Asn Arg Leu
        130                 135                 140

Arg Leu Ala Pro Ile Arg Asp Asp Gly Thr Ile Thr His Val Ile
145                 150                 155                 160

Gly Ile Gln Val Phe Ser Glu Thr Thr Ile Asp Leu Asp Arg Val Ser
                165                 170                 175

Tyr Pro Val Phe Lys His Lys Gln Gln Leu Asp Gln Thr Ser Glu Cys
                180                 185                 190

Leu Phe Pro Ser Gly Ser Pro Arg Phe Lys Glu His His Glu Asp Phe
            195                 200                 205

Cys Gly Ile Leu Gln Leu Ser Asp Glu Val Leu Ala His Asn Ile Leu
        210                 215                 220

Ser Arg Leu Thr Pro Arg Asp Val Ala Ser Ile Gly Ser Ala Cys Arg
225                 230                 235                 240

Arg Leu Arg Gln Leu Thr Lys Asn Glu Ser Val Arg Lys Met Val Cys
                245                 250                 255

Gln Asn Ala Trp Gly Lys Glu Ile Thr Gly Thr Leu Glu Ile Met Thr
                260                 265                 270

Lys Lys Leu Arg Trp Gly Arg Leu Ala Arg Glu Leu Thr Thr Leu Glu
            275                 280                 285

Ala Val Cys Trp Arg Lys Phe Thr Val Gly Gly Ile Val Gln Pro Ser
        290                 295                 300

Arg Cys Asn Phe Ser Ala Cys Ala Val Gly Asn Arg Leu Val Leu Phe
305                 310                 315                 320

Gly Gly Glu Gly Val Asn Met Gln Pro Leu Asp Asp Thr Phe Val Leu
                325                 330                 335
```

```
Asn Leu Asp Ala Glu Cys Pro Glu Trp Gln Arg Val Arg Val Thr Ser
            340                 345                 350

Ser Pro Pro Gly Arg Trp Gly His Thr Leu Ser Cys Leu Asn Gly Ser
        355                 360                 365

Trp Leu Val Val Phe Gly Gly Cys Gly Arg Gln Gly Leu Leu Asn Asp
    370                 375                 380

Val Phe Val Leu Asp Leu Asp Ala Lys His Pro Thr Trp Lys Glu Val
385                 390                 395                 400

Ala Gly Gly Thr Pro Pro Leu Pro Arg Ser Trp His Ser Ser Cys Thr
                405                 410                 415

Ile Glu Gly Ser Lys Leu Val Val Ser Gly Gly Cys Thr Asp Ala Gly
            420                 425                 430

Val Leu Leu Ser Asp Thr Phe Leu Leu Asp Leu Thr Thr Asp Lys Pro
        435                 440                 445

Thr Trp Lys Glu Ile Pro Thr Ser Trp Ala Pro Pro Ser Arg Leu Gly
    450                 455                 460

His Ser Leu Ser Val Phe Gly Arg Thr Lys Ile Leu Met Phe Gly Gly
465                 470                 475                 480

Leu Ala Asn Ser Gly His Leu Lys Leu Arg Ser Gly Glu Ala Tyr Thr
                485                 490                 495

Ile Asp Leu Glu Asp Glu Pro Arg Trp Arg Glu Leu Glu Cys Ser
            500                 505                 510

Ala Phe Pro Gly Val Val Val Pro Pro Arg Leu Asp His Val Ala
        515                 520                 525

Val Ser Met Pro Cys Gly Arg Val Ile Phe Gly Gly Ser Ile Ala
530                 535                 540

Gly Leu His Ser Pro Ser Gln Leu Phe Leu Ile Asp Pro Ala Glu Glu
545                 550                 555                 560

Lys Pro Ser Trp Arg Ile Leu Asn Val Pro Gly Lys Pro Pro Lys Leu
                565                 570                 575

Ala Trp Gly His Ser Thr Cys Val Val Gly Gly Thr Arg Val Leu Val
            580                 585                 590

Leu Gly Gly His Thr Gly Glu Glu Trp Ile Leu Asn Glu Leu His Glu
        595                 600                 605

Leu Cys Leu Ala Ser Arg Gln Asp Ser Asp Leu
    610                 615
```

<210> SEQ ID NO 3
<211> LENGTH: 168
<212> TYPE: PRT
<213> ORGANISM: Arabidopsis thaliana

<400> SEQUENCE: 3

```
Met Ala Arg Glu His Ala Ile Gly Glu Ala Thr Gly Lys Arg Lys Lys
  1               5                  10                  15

Arg Gly Arg Val Glu Glu Ala Glu Glu Tyr Cys Asn Asp Gly Ile Glu
                20                  25                  30

Glu Gln Val Glu Asp Glu Lys Leu Pro Leu Glu Val Gly Met Phe Tyr
            35                  40                  45

Tyr Pro Met Thr Pro Pro Ser Phe Ile Val Ser Asp Ala Leu Glu Pro
    50                  55                  60

Asp Phe Pro Leu Ile Tyr Val Asn Arg Val Phe Glu Val Phe Thr Gly
65                  70                  75                  80

Tyr Arg Ala Asp Glu Val Leu Gly Arg Asn Cys Arg Phe Leu Gln Tyr
                85                  90                  95
```

```
Arg Asp Pro Arg Ala Gln Arg Arg His Pro Leu Val Asp Pro Val Val
            100                 105                 110

Val Ser Glu Ile Arg Arg Cys Leu Glu Glu Gly Ile Glu Phe Gln Gly
        115                 120                 125

Glu Leu Leu Asn Phe Arg Lys Asp Gly Thr Pro Leu Val Asn Arg Leu
    130                 135                 140

Arg Leu Ala Pro Ile Arg Asp Asp Asp Gly Thr Ile Thr His Val Ile
145                 150                 155                 160

Gly Ile Gln Val Phe Ser Glu Thr
                165

<210> SEQ ID NO 4
<211> LENGTH: 3522
<212> TYPE: DNA
<213> ORGANISM: Arabidopsis thaliana

<400> SEQUENCE: 4
```

| | | | | | |
|---|---|---|---|---|---|
| atggctagtt | catcttcatc | tgagagatgg | atcgatggtc | ttcagttctc | ttccttgtta | 60 |
| tggcctccgc | cacgagatcc | tcaacaacat | aaggatcaag | tcgttgctta | tgttgaatat | 120 |
| tttggtcaat | ttacatcaga | gcaattccca | gatgacattg | ctgagttggt | ccggcatcag | 180 |
| tatccatcaa | ccgagaagcg | acttttggac | gatgtgctgg | cgatgtttgt | ccttcatcat | 240 |
| ccggagcatg | tcatgcagt | cattcttcca | atcatttcat | gtcttattga | tggctcgttg | 300 |
| gtgtacagca | aggaagctca | tccgtttgcc | tctttcatat | ctttagtttg | cccaagtagt | 360 |
| gagaatgact | attcggagca | atgggctttg | gcatgtggag | aaatccttcg | catttttgact | 420 |
| cattacaacc | gtcccattta | taaaactgag | cagcaaaatg | gagatacaga | gagaaattgt | 480 |
| ctgagcaaag | ctacaactag | tggttctccg | acttcagagc | ctaaggctgg | atcaccaaca | 540 |
| cagcatgaaa | ggaaaccttt | aaggcctttg | tctccatgga | tcagtgatat | actacttgct | 600 |
| gctcctcttg | gtataagaag | tgactatttc | cgatggtgta | gtggtgtaat | gggtaaaatat | 660 |
| gctgctggag | agctcaagcc | gccaaccatt | gcttctcgag | gatctggtaa | acatcctcaa | 720 |
| ctgatgcctt | caaccccaag | atgggctgtt | gctaatggag | ctggtgtcat | actgagtgtt | 780 |
| tgtgatgatg | aagttgctcg | atatgagact | gctacgctga | cagcggtcgc | tgtccctgca | 840 |
| cttcttcttc | ctccgccaac | gacatcctta | tgatgagcatc | tagttgctgg | ccttccagct | 900 |
| cttgaaccat | atgcacgttt | gtttcataga | tactatgcca | ttgcaactcc | aagtgctacg | 960 |
| cagagacttc | ttcttggact | cttagaagca | ccaccgtcgt | gggctccaga | tgcacttgat | 1020 |
| gctgctgtac | agcttgtgga | actccttcga | gctgctgaag | attatgcatc | tggtgtaagg | 1080 |
| ctacccagga | actggatgca | tttgcacttc | ttgcgggcta | taggaattgc | tatgtctatg | 1140 |
| agggcaggtg | ttgctgctga | tgctgcagcc | gctttgcttt | tccgcatact | ctcacagccg | 1200 |
| gcactgcttt | ttcctccgct | aagtcaagtt | gagggagtag | aaattcagca | cgcgcctatt | 1260 |
| ggtggctaca | gttcaaatta | cagaaaacag | atagaagttc | ctgcagcaga | agcaaccatt | 1320 |
| gaagccactg | cccaaggaat | tgcctcaatg | ctttgtgctc | atggtcctga | agttgagtgg | 1380 |
| agaatttgca | ctatatggga | agctgcttat | ggtttgatcc | cttaaattc | ttcgcgggtt | 1440 |
| gatcttcccg | aaatcatagt | tgctaccccca | ctgcaacctc | ctatcttgtc | atggaattta | 1500 |
| tacattccac | tcctcaaagt | acttgaatat | cttccacggg | ggagtccttc | ggaagcatgc | 1560 |
| ttgatgaaaa | tatttgttgc | cactgtggaa | acaatactca | gtagaacttt | tccgcctgaa | 1620 |
| tcttccaggg | aactaaccag | aaaagctaga | tcgagtttta | ccacaagatc | agcgaccaaa | 1680 |

-continued

```
aatcttgcta tgtctgagct tcgtgctatg gtccatgctc tcttttaga atcatgcgct    1740
ggtgtggaat tagcttcacg cctacttttt gttgtgttga ctgtatgtgt tagccatgaa    1800
gcacagtcta gtggtagcaa gagaccgaga agtgaatatg ctagtactac tgaaaatatt    1860
gaggcgaatc aacctgtatc taacaatcaa actgctaacc gtaaaagtag gaatgtcaag    1920
ggacagggac ctgtggcagc atttgattca tacgttcttg ctgctgtttg tgctcttgcc    1980
tgtgaggttc agctgtatcc tatgatctct ggtgggggga acttttccaa ttctgccgtg    2040
gctggaacta ttacaaagcc tgtaaagata aatgggtcat ctaaagagta tggagctggg    2100
attgactcgg caattagtca tacgcgccga attttggcaa tcctagaggc actcttttca    2160
ttaaaaccat cttctgtggg gactccatgg agttacagtt ctagtgagat agttgctgcg    2220
gccatggttg cagctcatat ttccgaactg ttcagacgtt caaaggcctt gacgcatgca    2280
ttgtctgggt tgatgagatg taagtgggat aaggaaattc ataaagagc atcatcatta    2340
tataacctca tagatgttca cagcaaagtt gttgcctcca ttgttgacaa agctgaaccc    2400
ttggaagcct accttaagaa tacaccggtt cagaaggatt ctgtgacctg tttaaactgg    2460
aaacaagaga acacatgtgc aagcaccaca tgctttgata cagcggtgac atccgcctca    2520
aggactgaaa tgaatccaag aggaaaccat aagtatgcta gacattcaga tgaaggctca    2580
ggaagaccct cagagaaggg tatcaaagat ttcctcttgg atgcttctga tctagcgaat    2640
ttcctcacag ctgatagact cgcagggttc tattgtggta cacaaaagct tttgaggtca    2700
gtgcttgcag agaaaccgga gctgtctttc tccgttgttt cactgttatg cacaaactg    2760
attgctgctc ctgaaatcca gcccaccgca gaaagcacct ctgcgcaaca aggatggaga    2820
caggttgttg atgcgctatg caatgtcgta tctgcaacgc cagcgaaagc agcagcagca    2880
gttgtccttc aggctgaaag ggagttgcag ccttggatcg ccaaagatga tgaagaaggc    2940
caaaaaatgt ggaaaatcaa ccaacggata gtcaaagtgt tggtggaact catgcgcaat    3000
catgacaggc ctgagtcact ggtgattctc gcaagtgcat cagatcttct tctgcgggca    3060
actgatggaa tgcttgttga tggagaagct tgtacattac ctcaacttga gctacttgaa    3120
gccacggcaa gagcaataca gccggtgcta gcttggggc catctggact agcagtggtc    3180
gacggtttat ccaatctatt gaagtgtcgt ctaccagcaa caatacggtg cctttcacac    3240
ccaagtgcac acgtacgtgc cttaagcacg tcagtactac gtgatatcat gaaccaaagc    3300
tccatacca tcaaagtaac tccaaaactg ccaacaacag agaagaacgg aatgaatagt    3360
ccgtcctatc gattcttcaa cgccgcctca atagactgga aagccgatat ccaaaactgt    3420
ttaaactggg aagctcacag cttgctctcc acaactatgc ctactcagtt tctcgacact    3480
gcggctcggg aactcggctg tactatatcc ttgtcccaat aa                      3522
```

<210> SEQ ID NO 5
<211> LENGTH: 1173
<212> TYPE: PRT
<213> ORGANISM: Arabidopsis thaliana

<400> SEQUENCE: 5

Met Ala Ser Ser Ser Ser Glu Arg Trp Ile Asp Gly Leu Gln Phe
 1               5                  10                  15

Ser Ser Leu Leu Trp Pro Pro Arg Asp Pro Gln Gln His Lys Asp
                20                  25                  30

Gln Val Val Ala Tyr Val Glu Tyr Phe Gly Gln Phe Thr Ser Glu Gln
            35                  40                  45

```
Phe Pro Asp Asp Ile Ala Glu Leu Val Arg His Gln Tyr Pro Ser Thr
 50                  55                  60

Glu Lys Arg Leu Leu Asp Val Leu Ala Met Phe Val Leu His His
 65                  70                  75                  80

Pro Glu His Gly His Ala Val Ile Leu Pro Ile Ile Ser Cys Leu Ile
                 85                  90                  95

Asp Gly Ser Leu Val Tyr Ser Lys Glu Ala His Pro Phe Ala Ser Phe
             100                 105                 110

Ile Ser Leu Val Cys Pro Ser Ser Glu Asn Asp Tyr Ser Glu Gln Trp
         115                 120                 125

Ala Leu Ala Cys Gly Glu Ile Leu Arg Ile Leu Thr His Tyr Asn Arg
     130                 135                 140

Pro Ile Tyr Lys Thr Glu Gln Gln Asn Gly Asp Thr Glu Arg Asn Cys
145                 150                 155                 160

Leu Ser Lys Ala Thr Thr Ser Gly Ser Pro Thr Ser Glu Pro Lys Ala
                 165                 170                 175

Gly Ser Pro Thr Gln His Glu Arg Lys Pro Leu Arg Pro Leu Ser Pro
             180                 185                 190

Trp Ile Ser Asp Ile Leu Leu Ala Ala Pro Leu Gly Ile Arg Ser Asp
         195                 200                 205

Tyr Phe Arg Trp Cys Ser Gly Val Met Gly Lys Tyr Ala Ala Gly Glu
    210                 215                 220

Leu Lys Pro Pro Thr Ile Ala Ser Arg Gly Ser Gly Lys His Pro Gln
225                 230                 235                 240

Leu Met Pro Ser Thr Pro Arg Trp Ala Val Ala Asn Gly Ala Gly Val
                245                 250                 255

Ile Leu Ser Val Cys Asp Asp Glu Val Ala Arg Tyr Glu Thr Ala Thr
            260                 265                 270

Leu Thr Ala Val Ala Val Pro Ala Leu Leu Pro Pro Thr Thr
        275                 280                 285

Ser Leu Asp Glu His Leu Val Ala Gly Leu Pro Ala Leu Glu Pro Tyr
    290                 295                 300

Ala Arg Leu Phe His Arg Tyr Tyr Ala Ile Ala Thr Pro Ser Ala Thr
305                 310                 315                 320

Gln Arg Leu Leu Leu Gly Leu Leu Glu Ala Pro Pro Ser Trp Ala Pro
                325                 330                 335

Asp Ala Leu Asp Ala Ala Val Gln Leu Val Glu Leu Leu Arg Ala Ala
            340                 345                 350

Glu Asp Tyr Ala Ser Gly Val Arg Leu Pro Arg Asn Trp Met His Leu
        355                 360                 365

His Phe Leu Arg Ala Ile Gly Ile Ala Met Ser Met Arg Ala Gly Val
    370                 375                 380

Ala Ala Asp Ala Ala Ala Leu Leu Phe Arg Ile Leu Ser Gln Pro
385                 390                 395                 400

Ala Leu Leu Phe Pro Pro Leu Ser Gln Val Glu Gly Val Glu Ile Gln
                405                 410                 415

His Ala Pro Ile Gly Gly Tyr Ser Ser Asn Tyr Arg Lys Gln Ile Glu
            420                 425                 430

Val Pro Ala Ala Glu Ala Thr Ile Glu Ala Thr Ala Gln Gly Ile Ala
        435                 440                 445

Ser Met Leu Cys Ala His Gly Pro Glu Val Glu Trp Arg Ile Cys Thr
450                 455                 460
```

```
Ile Trp Glu Ala Ala Tyr Gly Leu Ile Pro Leu Asn Ser Ser Ala Val
465                 470                 475                 480

Asp Leu Pro Glu Ile Ile Val Ala Thr Pro Leu Gln Pro Pro Ile Leu
            485                 490                 495

Ser Trp Asn Leu Tyr Ile Pro Leu Leu Lys Val Leu Glu Tyr Leu Pro
            500                 505                 510

Arg Gly Ser Pro Ser Glu Ala Cys Leu Met Lys Ile Phe Val Ala Thr
            515                 520                 525

Val Glu Thr Ile Leu Ser Arg Thr Phe Pro Pro Glu Ser Ser Arg Glu
        530                 535                 540

Leu Thr Arg Lys Ala Arg Ser Ser Phe Thr Thr Arg Ser Ala Thr Lys
545                 550                 555                 560

Asn Leu Ala Met Ser Glu Leu Arg Ala Met Val His Ala Leu Phe Leu
                565                 570                 575

Glu Ser Cys Ala Gly Val Glu Leu Ala Ser Arg Leu Leu Phe Val Val
                580                 585                 590

Leu Thr Val Cys Val Ser His Glu Ala Gln Ser Ser Gly Ser Lys Arg
            595                 600                 605

Pro Arg Ser Glu Tyr Ala Ser Thr Thr Glu Asn Ile Glu Ala Asn Gln
610                 615                 620

Pro Val Ser Asn Asn Gln Thr Ala Asn Arg Lys Ser Arg Asn Val Lys
625                 630                 635                 640

Gly Gln Gly Pro Val Ala Ala Phe Asp Ser Tyr Val Leu Ala Ala Val
                645                 650                 655

Cys Ala Leu Ala Cys Glu Val Gln Leu Tyr Pro Met Ile Ser Gly Gly
                660                 665                 670

Gly Asn Phe Ser Asn Ser Ala Val Ala Gly Thr Ile Thr Lys Pro Val
            675                 680                 685

Lys Ile Asn Gly Ser Ser Lys Glu Tyr Gly Ala Gly Ile Asp Ser Ala
690                 695                 700

Ile Ser His Thr Arg Arg Ile Leu Ala Ile Leu Glu Ala Leu Phe Ser
705                 710                 715                 720

Leu Lys Pro Ser Ser Val Gly Thr Pro Trp Ser Tyr Ser Ser Ser Glu
                725                 730                 735

Ile Val Ala Ala Ala Met Val Ala Ala His Ile Ser Glu Leu Phe Arg
                740                 745                 750

Arg Ser Lys Ala Leu Thr His Ala Leu Ser Gly Leu Met Arg Cys Lys
            755                 760                 765

Trp Asp Lys Glu Ile His Lys Arg Ala Ser Ser Leu Tyr Asn Leu Ile
770                 775                 780

Asp Val His Ser Lys Val Val Ala Ser Ile Val Asp Lys Ala Glu Pro
785                 790                 795                 800

Leu Glu Ala Tyr Leu Lys Asn Thr Pro Val Gln Lys Asp Ser Val Thr
                805                 810                 815

Cys Leu Asn Trp Lys Gln Glu Asn Thr Cys Ala Ser Thr Thr Cys Phe
            820                 825                 830

Asp Thr Ala Val Thr Ser Ala Arg Thr Glu Met Asn Pro Arg Gly
            835                 840                 845

Asn His Lys Tyr Ala Arg His Ser Asp Glu Gly Ser Gly Arg Pro Ser
            850                 855                 860

Glu Lys Gly Ile Lys Asp Phe Leu Leu Asp Ala Ser Asp Leu Ala Asn
865                 870                 875                 880

Phe Leu Thr Ala Asp Arg Leu Ala Gly Phe Tyr Cys Gly Thr Gln Lys
```

885                 890                 895
Leu Leu Arg Ser Val Leu Ala Glu Lys Pro Glu Leu Ser Phe Ser Val
                900                 905                 910

Val Ser Leu Leu Trp His Lys Leu Ile Ala Pro Glu Ile Gln Pro
                915                 920                 925

Thr Ala Glu Ser Thr Ser Ala Gln Gln Gly Trp Arg Gln Val Val Asp
        930                 935                 940

Ala Leu Cys Asn Val Val Ser Ala Thr Pro Ala Lys Ala Ala Ala
945                 950                 955                 960

Val Val Leu Gln Ala Glu Arg Glu Leu Gln Pro Trp Ile Ala Lys Asp
                965                 970                 975

Asp Glu Glu Gly Gln Lys Met Trp Lys Ile Asn Gln Arg Ile Val Lys
            980                 985                 990

Val Leu Val Glu Leu Met Arg Asn His Asp Arg Pro Glu Ser Leu Val
            995                 1000                1005

Ile Leu Ala Ser Ala Ser Asp Leu Leu Leu Arg Ala Thr Asp Gly Met
        1010                1015                1020

Leu Val Asp Gly Glu Ala Cys Thr Leu Pro Gln Leu Glu Leu Leu Glu
1025                1030                1035                1040

Ala Thr Ala Arg Ala Ile Gln Pro Val Leu Ala Trp Gly Pro Ser Gly
                1045                1050                1055

Leu Ala Val Val Asp Gly Leu Ser Asn Leu Leu Lys Cys Arg Leu Pro
            1060                1065                1070

Ala Thr Ile Arg Cys Leu Ser His Pro Ser Ala His Val Arg Ala Leu
        1075                1080                1085

Ser Thr Ser Val Leu Arg Asp Ile Met Asn Gln Ser Ser Ile Pro Ile
    1090                1095                1100

Lys Val Thr Pro Lys Leu Pro Thr Thr Glu Lys Asn Gly Met Asn Ser
1105                1110                1115                1120

Pro Ser Tyr Arg Phe Phe Asn Ala Ala Ser Ile Asp Trp Lys Ala Asp
                1125                1130                1135

Ile Gln Asn Cys Leu Asn Trp Glu Ala His Ser Leu Leu Ser Thr Thr
            1140                1145                1150

Met Pro Thr Gln Phe Leu Asp Thr Ala Ala Arg Glu Leu Gly Cys Thr
        1155                1160                1165

Ile Ser Leu Ser Gln
        1170

<210> SEQ ID NO 6
<211> LENGTH: 100
<212> TYPE: PRT
<213> ORGANISM: Arabidopsis thaliana

<400> SEQUENCE: 6

Met Ala Ser Ser Ser Ser Glu Arg Trp Ile Asp Gly Leu Gln Phe
1               5                   10                  15

Ser Ser Leu Leu Trp Pro Pro Arg Asp Pro Gln His Lys Asp
            20                  25                  30

Gln Val Val Ala Tyr Val Glu Tyr Phe Gly Gln Phe Thr Ser Glu Gln
        35                  40                  45

Phe Pro Asp Asp Ile Ala Glu Leu Val Arg His Gln Tyr Pro Ser Thr
    50                  55                  60

Glu Lys Arg Leu Leu Asp Asp Val Leu Ala Met Phe Val Leu His His
65                  70                  75                  80

```
Pro Glu His Gly His Ala Val Ile Leu Pro Ile Ile Ser Cys Leu Ile
            85                  90                  95

Asp Gly Ser Leu
           100
```